US00RE51082E

(19) United States
(12) Reissued Patent
Connell et al.

(10) Patent Number: US RE51,082 E
(45) Date of Reissued Patent: Oct. 20, 2026

(54) MEDICAMENT DISPENSER

(71) Applicant: Glaxo Group Limited, Stevenage (GB)

(72) Inventors: Hugh Alexander Connell, Worcestershire (GB); Stephen James Harvey, Hertfordshire (GB); Robert William Tansley, Warwickshire (GB)

(73) Assignee: Glaxo Group Limited (GB)

(21) Appl. No.: 19/284,004

(22) Filed: Jul. 29, 2025

Related U.S. Patent Documents

Reissue of:

(64) Patent No.: 8,746,242
Issued: Jun. 10, 2014
Appl. No.: 11/996,762
PCT Filed: Jul. 27, 2006
PCT No.: PCT/GB2006/002831
§ 371 (c)(1),
(2) Date: Jan. 25, 2008
PCT Pub. No.: WO2007/012871
PCT Pub. Date: Feb. 1, 2007

(30) Foreign Application Priority Data

Jul. 28, 2005 (GB) ..... 0515584

(51) Int. Cl.
*A61M 15/00* (2006.01)

(52) U.S. Cl.
CPC .... *A61M 15/0045* (2013.01); *A61M 15/0003* (2014.02); *A61M 15/0025* (2014.02);
(Continued)

(58) Field of Classification Search
CPC ..... A61M 15/0025; A61M 15/0026; A61M 2202/064
See application file for complete search history.

(56) References Cited

U.S. PATENT DOCUMENTS 3,269,389 A 8/1966 Meurer et al.
4,570,769 A 2/1986 Isaka
(Continued)

FOREIGN PATENT DOCUMENTS

DE 1461280 A1 2/1969
EP 0469814 A1 2/1992
(Continued)

OTHER PUBLICATIONS

*Glaxo Group Limited et al.* v. *Transpire Bio Inc.*, 0:25-cv-61939 (S.D. Fla). Complaint.
(Continued)

*Primary Examiner* — William E Dondero
(74) *Attorney, Agent, or Firm* — J. Scott Young

(57) ABSTRACT

A medicament dispenser for use with at least one medicament carrier carrying multiple distinct medicament portions, said medicament dispenser comprising (a) a dispensing mechanism actuable for dispensing the distinct medicament portions carried by the at least one medicament carrier;
(b) a mouthpiece; and
(c) a cover for the mouthpiece, the cover being movably mounted to the dispenser for sequential movement from a first position, in which the mouthpiece is covered, to a second position, in which the mouthpiece is at least part-uncovered, to a third position in which the mouthpiece is uncovered;

wherein the cover is adapted to couple with the dispensing mechanism such that movement of the cover from the
(Continued)

second position to the third position, but not the first position to the second position, results in actuation of the dispensing mechanism.

38 Claims, 19 Drawing Sheets

(52) U.S. Cl.
CPC .... *A61M 15/0043* (2014.02); *A61M 15/0051* (2014.02); *A61M 15/0055* (2014.02); *A61M 15/007* (2014.02); *A61M 15/0075* (2014.02); *A61M 2202/064* (2013.01)

(56) References Cited

U.S. PATENT DOCUMENTS

| | | | |
|---|---|---|---|
| 4,735,358 | A | 4/1988 | Morita et al. |
| 4,811,731 | A | 3/1989 | Newell et al. |
| 4,860,419 | A | 8/1989 | Hekman |
| 4,940,966 | A | 7/1990 | Pettigrew et al. |
| 5,002,048 | A | 3/1991 | Makiej, Jr. |
| 5,007,419 | A | 4/1991 | Weinstein et al. |
| 5,263,475 | A | 11/1993 | Altermatt et al. |
| 5,320,095 | A | 6/1994 | Nijkerk et al. |
| 5,437,267 | A | 8/1995 | Weinstein et al. |
| 5,462,205 | A | 10/1995 | Keller |
| 5,497,765 | A | 3/1996 | Praud et al. |
| 5,505,704 | A | 4/1996 | Pawelka et al. |
| 5,590,645 | A | 1/1997 | Davies et al. |
| 5,619,984 | A | 4/1997 | Hodson et al. |
| 5,664,557 | A | 9/1997 | Makiej, Jr. |
| 5,740,793 | A | 4/1998 | Hodson et al. |
| 5,772,085 | A | 6/1998 | Bryant et al. |
| 5,787,881 | A | 8/1998 | Chawla |
| 5,830,490 | A | 11/1998 | Weinstein et al. |
| 5,860,419 | A | 1/1999 | Davies et al. |
| 5,873,360 | A | 2/1999 | Davies et al. |
| 5,921,237 | A | 7/1999 | Eisele et al. |
| 5,941,241 | A | 8/1999 | Weinstein et al. |
| 5,998,428 | A | 12/1999 | Barnette et al. |
| 6,029,663 | A | 2/2000 | Eisele et al. |
| 6,102,179 | A | 8/2000 | Hodson et al. |
| 6,116,237 | A | 9/2000 | Schultz et al. |
| 6,182,655 | B1 | 2/2001 | Keller et al. |
| 6,610,873 | B2 | 8/2003 | Saito |
| 6,810,873 | B1 | 11/2004 | Haikarainen et al. |
| 6,889,690 | B2 | 5/2005 | Crowder et al. |
| 7,077,129 | B2 | 7/2006 | Anderson et al. |
| 8,161,968 | B2 | 4/2012 | Augustyn et al. |
| 2001/0027789 | A1 | 10/2001 | Goede et al. |
| 2002/0040713 | A1 | 4/2002 | Eisele et al. |
| 2002/0078949 | A1 | 6/2002 | Leary |
| 2003/0183230 | A1 | 10/2003 | Nelson et al. |
| 2004/0050864 | A1 | 3/2004 | Stradella |
| 2005/0126568 | A1 | 6/2005 | Davies et al. |
| 2005/0154491 | A1 | 7/2005 | Anderson et al. |
| 2005/0172964 | A1 | 8/2005 | Anderson et al. |
| 2006/0196504 | A1 | 9/2006 | Augustyn et al. |
| 2006/0239932 | A1 | 10/2006 | Monteith et al. |

FOREIGN PATENT DOCUMENTS

| | | | |
|---|---|---|---|
| EP | 0521434 | A1 | 1/1993 |
| EP | 0751077 | A1 | 1/1997 |
| EP | 1300171 | A2 | 4/2003 |
| GB | 1387954 | A | 3/1975 |
| GB | 2242134 | A | 9/1991 |
| GB | 2327408 | A | 1/1999 |
| JP | 58091932 | A | 6/1983 |
| JP | S5891932 | A | 6/1983 |
| JP | 5103835 | A | 4/1993 |
| JP | H05103835 | A | 4/1993 |
| JP | 2003518418 | A | 6/2003 |
| WO | 9212402 | A1 | 7/1992 |
| WO | WO-1992012402 | A1 | 7/1992 |
| WO | 9514867 | A1 | 6/1995 |
| WO | WO-1995014867 | A1 | 6/1995 |
| WO | 9631790 | A1 | 10/1996 |
| WO | WO-1996031790 | A1 | 10/1996 |
| WO | 9834664 | A1 | 6/1998 |
| WO | 9830332 | A2 | 7/1998 |
| WO | WO-1998030332 | A2 | 7/1998 |
| WO | WO-1998034664 | A1 | 8/1998 |
| WO | 9851257 | A1 | 11/1998 |
| WO | WO-1998051257 | A1 | 11/1998 |
| WO | 9939991 | A1 | 8/1999 |
| WO | WO-1999039991 | A1 | 8/1999 |
| WO | 0000411 | A1 | 1/2000 |
| WO | WO-2000000411 | A1 | 1/2000 |
| WO | 0045879 | A1 | 8/2000 |
| WO | WO-2000045879 | A1 | 8/2000 |
| WO | 0051599 | A1 | 9/2000 |
| WO | WO-2000051599 | A1 | 9/2000 |
| WO | 0064519 | A1 | 11/2000 |
| WO | 0064520 | A1 | 11/2000 |
| WO | WO-2000064519 | A1 | 11/2000 |
| WO | WO-2000064520 | A1 | 11/2000 |
| WO | 0117595 | A1 | 3/2001 |
| WO | WO-2001017595 | A1 | 3/2001 |
| WO | 0124690 | A2 | 4/2001 |
| WO | 0126020 | A1 | 4/2001 |
| WO | 0126021 | A1 | 4/2001 |
| WO | 0126720 | A1 | 4/2001 |
| WO | WO-2001024690 | A2 | 4/2001 |
| WO | WO-2001026020 | A1 | 4/2001 |
| WO | WO-2001026021 | A1 | 4/2001 |
| WO | WO-2001026720 | A1 | 4/2001 |
| WO | 0139823 | A1 | 6/2001 |
| WO | 0141849 | A2 | 6/2001 |
| WO | WO-2001039823 | A1 | 6/2001 |
| WO | WO-2001041849 | A2 | 6/2001 |
| WO | 0168169 | A1 | 9/2001 |
| WO | WO-2001068169 | A1 | 9/2001 |
| WO | 0197886 | A1 | 12/2001 |
| WO | 0198176 | A2 | 12/2001 |
| WO | WO-2001097886 | A1 | 12/2001 |
| WO | WO-2001098176 | A2 | 12/2001 |
| WO | 0200279 | A1 | 1/2002 |
| WO | 0204055 | A1 | 1/2002 |
| WO | WO-2002000279 | A1 | 1/2002 |
| WO | WO-2002004055 | A1 | 1/2002 |
| WO | 0224268 | A1 | 3/2002 |
| WO | WO-2002024268 | A1 | 3/2002 |
| WO | 02053294 | A1 | 7/2002 |
| WO | WO-2002053294 | A1 | 7/2002 |
| WO | 2003/024439 | A1 | 3/2003 |
| WO | 03024514 | A1 | 3/2003 |
| WO | WO-2003024514 | A1 | 3/2003 |
| WO | 03061743 | A1 | 7/2003 |
| WO | 03080149 | A2 | 10/2003 |
| WO | WO-2003080149 | A2 | 10/2003 |
| WO | 2003/090811 | A2 | 11/2003 |
| WO | 2003/090825 | A1 | 11/2003 |
| WO | 03090825 | A1 | 11/2003 |
| WO | 03095010 | A2 | 11/2003 |
| WO | 2004011070 | A1 | 2/2004 |
| WO | 2004012801 | A1 | 2/2004 |
| WO | 2004054646 | A1 | 7/2004 |
| WO | 2005/002654 | A2 | 1/2005 |
| WO | 2005/016424 | A2 | 2/2005 |
| WO | 2005014089 | A1 | 2/2005 |
| WO | 2005037353 | A1 | 4/2005 |
| WO | 2005/046636 | A1 | 5/2005 |
| WO | 2005079727 | A2 | 9/2005 |
| WO | 2005/104745 | A2 | 11/2005 |
| WO | 2006018261 | A1 | 2/2006 |
| WO | 2006/066908 | A1 | 6/2006 |
| WO | 2006/066909 | A1 | 6/2006 |
| WO | 2007012871 | A1 | 2/2007 |

(56) References Cited

FOREIGN PATENT DOCUMENTS

| | | | |
|---|---|---|---|
| WO | 2007/134964 | A1 | 11/2007 |
| WO | 2007/135024 | A1 | 11/2007 |

OTHER PUBLICATIONS

*Glaxo Group Limited et al.* v. *Transpire Bio Inc.*, 0:25-cv-61939 (S.D. Fla). Defendant's Answer, Separate Defenses, and Counterclaims to Plaintiffs' Complaint.

*Glaxo Group Limited et al.* v. *Transpire Bio Inc.*, 0:26-cv-60696 (S.D. Fla). Complaint.

*Glaxo Group Limited et al.* v. *Transpire Bio Inc.*, 0:26-cv-60696 (S.D. Fla). Defendant's Answer, Separate Defenses, and Counterclaims to Plaintiffs' Complaint.

*Glaxo Group Limited et al.* v. *Transpire Bio Inc.*, 0:25-cv-61939 (S.D. Fla). Defendant's Preliminary Invalidity Contentions.

Discovery of novel 1-azoniabicyclo[2.2.2]octane muscarinic acetylcholine receptor antagonists, J. Med. Chem. 2009, 52(8), 2493-505 ("Laine").

Co-Pending U.S. Appl. No. 19/283,933, filed Jul. 29, 2025, 60 Pages.

Co-Pending U.S. Appl. No. 19/284,004, filed Jul. 29, 2025, 39 Pages.

Restriction Requirement dated Oct. 6, 2009 for U.S. Appl. No. 10/565,515.

Amendment filed Oct. 26, 2009 in response to Restriction Requirement dated Oct. 6, 2009 for U.S. Appl. No. 10/565,515.

Non-Final Office Action dated Jan. 5, 2010 for U.S. Appl. No. 10/565,515.

Amendment filed Jun. 4, 2010 in response to Non-Final Office Action dated Jan. 5, 2010 for U.S. Appl. No. 10/565,515.

Notice of Allowance dated Sep. 14, 2010 for U.S. Appl. No. 10/565,515.

Request for Continued Examination filed Dec. 7, 2010 in response to Notice of Allowance dated Sep. 14, 2010 for U.S. Appl. No. 10/565,515.

Notice of Allowance dated Dec. 17, 2010 for U.S. Appl. No. 10/565,515.

Request for Continued Examination filed Mar. 16, 2011 in response to Notice of Allowance dated Dec. 17, 2010 for U.S. Appl. No. 10/565,515.

Notice of Allowance dated Apr. 4, 2011 for U.S. Appl. No. 10/565,515.

-- PRIOR ART --

MEDICAMENT DISPENSER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATION

This application is filed pursuant to 35 USC 371 as a U. S. National Phase Application of International Patent Application Ser. No. PCT/GB2006/002831 filed on 27 Jul. 2006, which claims priority from GB Priority Application No. 0515584.1 filed on 28 Jul. 2005 in the United Kingdom.

TECHNICAL FIELD

The present invention relates to a medicament dispenser for dispensing medicament. The invention particularly relates to a dispenser for use in dispensing medicament in powder or tablet form.

BACKGROUND TO THE INVENTION

The use of inhalation devices in the administration of medicaments, for example in bronchodilation therapy is well known. Such devices generally comprise a body or housing within which a medicament carrier is located. Known inhalation devices include those in which the medicament carrier is a blister strip containing a number of discrete doses of powdered medicament. Such devices usually contain a mechanism of accessing these doses, usually comprising either piercing means or means to peel a lid sheet away from a base sheet. The powdered medicament can then be accessed and inhaled. Such a mechanism may also be used for dispensing medicament in tablet form wherein peeling away the lid sheet from the base sheet reveals a tablet for removal and subsequent consumption.

With such devices access to each dose is typically enabled on a serial basis by advancing the strip within the device to sequentially bring each discrete dose of medicament carried by the strip to an opening station. Known devices, including that sold under the trademark DISKUS® by GlaxoSmithKline Plc, typically comprise a user-actuable lever mechanism coupled to a strip advancement mechanism (e.g. via a gear train). Thus, the user actuates the lever to advance the strip thereby causing the next discrete dose of medicament to be made available at the opening station.

Such devices also typically comprise a mouthpiece through which a user inhales to achieve inhaled delivery of the discrete medicament dose. It is desirable that a protective cover is provided to the mouthpiece to prevent contamination by dirt or dust particles. In use, the mouthpiece cover is removed by the user to reveal the mouthpiece before inhaling therethrough. Certain devices, including the DISKUS® inhalation device of GlaxoSmithKline Plc, have a mouthpiece cover that is attached to a housing of the device and reversibly movable (e.g. by pivotal movement) from a position, in which the mouthpiece is covered to one in which the mouthpiece is uncovered.

The Applicant has appreciated that it is potentially desirable from the standpoint of minimizing the number of steps required to ready the device for action to couple the movement of the mouthpiece cover to reveal the mouthpiece with actuation of the lever to advance the strip within the device. The Applicant has however, also appreciated a potential problem in that the user may desire to open the cover to reveal the mouthpiece for cleaning etc. but not wish by that action to also result in advancement of the dose. In solution to this problem, Applicant has now devised a device having a movable mouthpiece cover that is sequentially movable from a first 'mouthpiece covered' position to an intermediate 'mouthpiece uncovered' position, but then further movable to engage a strip advancement mechanism to cause advancement of the strip within the device.

SUMMARY OF THE INVENTION

According to one aspect of the present invention there is provided a medicament dispenser for use with at least one medicament carrier carrying multiple distinct medicament portions, said medicament dispenser comprising (a) a dispensing mechanism actuable for dispensing the distinct medicament portions carried by said at least one medicament carrier;

(b) a mouthpiece; and (c) a cover for said mouthpiece, said cover being movably mounted to the dispenser for sequential movement from a first position, in which said mouthpiece is covered, to a second position, in which said mouthpiece is at least part-uncovered, to a third position in which said mouthpiece is uncovered;

wherein said cover is adapted to couple with said dispensing mechanism such that movement of the cover from the second position to the third position, but not the first position to the second position, results in actuation of the dispensing mechanism.

According to another aspect of the invention there is provided a medicament dispenser for use with one or more elongate form medicament carriers, each having multiple distinct medicament dose portions carried thereby, said medicament dispenser comprising (a) a housing;

(b) within said housing, a dispensing mechanism for dispensing the distinct medicament dose portions carried by each of said one or more medicament carriers, said dispensing mechanism comprising i) a receiving station for receiving each of the one or more medicament carriers;

ii) a release for releasing a distinct medicament dose portion from each of the one or more medicament carriers on receipt thereof by said receiving station;

iii) an outlet, in communication with said distinct medicament dose portion of each of the one or more medicament carriers releasable by said release; and iv) an indexer for individually indexing the distinct medicament dose portions of each of the one or more medicament carriers;

(c) provided to the housing, a mouthpiece, capable of communication with said outlet; and (d) in movable connection to the housing, a cover for said mouthpiece, said cover being movable from a first position, in which said mouthpiece is covered, to a second position, in which said mouthpiece is at least part-uncovered, wherein said cover is capable of coupling with said dispensing mechanism such that further movement of the cover from the second position to a third position results in actuation of the dispensing mechanism.

The medicament dispenser of the present invention is preferably a hand-held, hand-operable dispenser.

The medicament dispenser of the present invention is preferably an inhaler, in particular a dry powder inhaler (DPI). Typically, the DPI will be of the breath-actuated type; i.e. patient inhalation at the mouthpiece creates an inspiratory airstream in/through the DPI which entrains medicament powder from the medicament carrier(s) into the patient's respiratory tract.

In a first embodiment herein, the medicament dispenser is designed to receive a single, optionally elongate form, medicament carrier.

In a second embodiment herein, the medicament dispenser is designed to receive plural, optionally elongate form, medicament carriers. Preferably, the medicament dispenser is designed to receive from two to four such medicament carriers, more preferably two such carriers. Suitably, in the context of this second embodiment, the distinct medicament dose portions releasable from each of the plural medicament carriers in combination comprise a defined dose of combination product. That is to say, that when combined together (e.g. on release) the distinct active medicament dose portions form a single dose of a 'multi-active' medicament treatment.

Suitable medicament carriers for use with the medicament dispenser herein have multiple distinct dose portions carried thereby. The distinct dose portions are typically arranged in spaced fashion, more preferably in progressive arrangement (e.g. series progression) on the carrier such that each dose portion is separately accessible.

The term medicament carrier herein is used to define any suitable form of carrier. Suitably, each elongate form medicament carrier is in the form of a strip or tape. In one preferred aspect, the carrier has a blister pack form, but it could also, for example, comprise a carrier onto which medicament has been applied by any suitable process including printing, painting and vacuum occlusion.

In one aspect, the medicament carrier comprises a blister pack in laminate form. Suitably, the laminate comprises material selected from the group consisting of metal foil, organic polymeric material and paper. Suitable metal foils include aluminium or tin foil having a thickness of from 5 to 100 μm, preferably from 10 to 50 μm, such as 20 to 30 μm. Suitable organic polymeric materials include polyethylene, polypropylene, polyvinyl chloride and polyethylene terephthalate.

Access to the medicament dose portions comprised within the pockets of the elongate strip form carrier is by any suitable access means including tearing, piercing or peeling apart the relevant pockets.

One suitable blister pack form medicament carrier comprises a peelable blister strip. Suitably, the peelable blister strip comprises a base sheet in which blisters are formed to define pockets therein for containing distinct medicament dose portions and a lid sheet which is hermetically sealed to the base sheet except in the region of the blisters in such a manner that the lid sheet and the base sheet can be peeled apart. The base and lid sheets are typically sealed to one another over their whole width except for the forward end portions where they are typically not sealed to one another at all. Thus, separate base and lid sheet forward end portions are presented at the end of the strip. The respective base and lid sheets are peelably separable from each other to (e.g. separately) release the contents of each pocket.

Suitably, the lid sheet comprises at least the following successive layers: (a) paper; adhesively bonded to (b) polyester; adhesively bonded to (c) aluminium foil; that is coated with a heat seal lacquer for bonding to the base sheet. The thickness of each layer may be selected according to the desired properties but is typically of the order of from 5 to 200 micron, particularly from 10 to 50 micron.

Suitably, the base sheet comprises at least the following successive layers: (a) oriented polyamide (OPA); adhesively bonded to (b) aluminium foil; adhesively bonded to (c) a third layer comprising a polymeric material (e.g. polyvinyl chloride).

Various known techniques can be employed to join the lid and base sheet and hence to seal the blisters of the peelable blister strip. Such methods include adhesive bonding, hot metal bonding, hot metal welding, radio frequency welding, laser welding, ultrasonic welding and hot bar sealing. The lid sheet and base sheet of the peelable blister strip are particularly sealable by 'cold form' sealing methods, which are conducted at lower temperatures than conventional heat sealing methods. Such 'cold form' sealing methods are of particular utility where the medicament or medicament formulation for containment within the blister is heat sensitive (e.g. degrades or denatures on heating). Suitable 'cold form' sealing methods are conducted at a temperature in the range of 150-250° C., more preferably, 210-240° C.

In one particular aspect, a first elongate form medicament carrier has multiple distinct mono-active medicament dose portions carried thereby and a second elongate form medicament carrier has multiple distinct plural-active (particularly, bi-active dose portions i.e. comprising two active components) medicament dose portions carried thereby. In combination, the mono-active and plural-active medicament components comprise a defined combination medicament product.

Suitably, the multiple distinct dose portions are provided to each medicament carrier in uniform series. In particular, the spacing (i.e. pitch) between each dose portion is uniform throughout the series. In other aspects however, the spacing (i.e. pitch) may vary throughout the series (i.e. be non-uniform). In specific examples, the pitch may progressively decrease or progressively increase throughout the series.

Where plural elongate form medicament carriers are provided to the medicament dispenser, these may be arranged in any suitable configuration. One preferred configuration is the 'side-by-side' configuration, in which for example, two carriers (e.g. two coiled blister strips) are arranged to lie in sideways alignment with each other in the dispenser. Another preferred configuration is the 'double-decker' configuration, in which for example, two carriers (e.g. two coiled blister strips sharing the same coiling axis) are arranged to lie one on top of each other in the dispenser.

The housing may take any suitable shape or form such as to accommodate the other features of the medicament dispenser. In one particular aspect, the housing takes the form of a shell comprising two shell halves that are joined to form the shell-form housing, as a whole.

Suitably, where the medicament dispenser is suitable for accommodating plural medicament carriers, some or all components of the dispensing mechanism are common for each of the medicament carriers. The advantage of having common components is that the number of separate parts in the medicament dispenser may be minimized.

In other aspects, the action of those components that are not common may in aspects, be suitably coupled. Coupling is achieved by any suitable fashion including mechanical linkages (e.g. co-gearing or via the use of coupling arms/rods) or electromechanical coupling controls. The advantage of coupling is that the indexing/advancement of each medicament carrier may be achieved in coupled fashion.

In other aspects, most or even all of the components of the dispensing mechanism are distinct. In one particular aspect, the dispenser is arranged such that each of the one or more medicament carriers can be indexed/advanced separately thereby providing the opportunity for complex dosing patterns in which any combination, or indeed any one, of the plural strips may be accessed.

Embodiments are envisaged both in which there is a single receiving station which is capable of receiving plural medicament carriers and also those in which each medicament carrier is received by a distinct (i.e. individual) receiving station. In the latter case, the individual receiving stations may either be coupled or not.

The release can have any suitable form. Where the elongate medicament carrier is in the form of a blister strip, the release may for example, comprise means to rupture, puncture, tear or otherwise access the blister. In a particular preferred aspect, where the medicament carrier is in the form of a peelable blister strip the release comprises means for peeling apart the blister strip. In one aspect herein, each blister strip is peeled apart about a defined beak or wedge form feature of the dispenser.

The outlet may have any suitable form, but in particular takes the form of a manifold or guiding released medicament dose to the mouthpiece.

The term 'mouthpiece' is used herein to mean an element through which the patient may inhale. In one aspect, that inhalation is by oral means with the patient placing the mouthpiece in its mouth. In an alternative aspect, the mouthpiece comprises a nozzle for insertion into the nasal cavity of a patient.

The outlet is preferably a single outlet, which communicates with the one or more distinct medicament portions on their release by said release. Communication is for example, via a common air channeling means (e.g. formed as an air-pipe or manifold) that communicates with the mouthpiece. The patient may therefore breathe in through the mouthpiece, and the breath then be transferred through the common air channeling means to the released medicament portion(s), thereby enabling inhalation of the medicament product.

The indexing by the indexer typically happens in sequential fashion, for example accessing portions sequentially arranged in series along the length of the elongate carrier. Where plural medicament carriers are present, the indexing of each carrier may be arranged to occur in coupled fashion, that is to say each is indexed concurrently.

In a preferred aspect, the medicament carrier comprises a peelable blister strip. In this aspect, the release suitably comprises a peeler for peeling apart a base sheet and lid sheet of each peelable strip to open a pocket. Suitably, the peeler includes lid driver for pulling apart a lid sheet from a base sheet of a pocket that has been received at the opening station.

Preferably, there is provided a medicament dispenser herein, for use with one or more blister strip form medicament carriers, each having multiple distinct pockets for containing medicament dose portions, wherein said pockets are spaced along the length of and defined between two peelable sheets secured to each other, in which he dispensing mechanism comprises a) an opening station for receiving a pocket of the one or more medicament carriers;

b) a peeler positioned to engage a base sheet and a lid sheet of a pocket which has been received in said opening station for peeling apart such a base sheet and lid sheet, to open such a pocket;

c) an outlet, positioned to be in communication with an opened pocket through which a user can access a medicament dose portion from such an opened pocket; and d) an indexer for individually indexing the distinct pockets of the one or more medicament carriers.

Suitably, where plural elongate medicament carriers are accommodated, a common opening station is provided for receiving a pocket of each of the plural medicament carriers. In another aspect, distinct opening stations are provided for receiving a pocket of each medicament carrier. Suitably, the distinct opening stations are linking by a communicating passageway or other means for enabling the coming together of the separately released medicaments.

Suitably, the one or more peelable strip form medicament carriers are acted on by a peeler (i.e. peeling means). The peeler engages a base sheet and a lid sheet of a pocket that has been received at the opening station(s) for peeling apart the base sheet and lid sheet to open a pocket. In one aspect, each peelable strip form medicament carrier is acted on by common peeler. In other aspects, each peelable strip is acted on by its own (i.e. separate) peeler.

Suitably, the peeler includes a lid driver for pulling apart a lid sheet and a base sheet of a pocket that has been received at the opening station.

In one aspect, the lid driver comprises a wheel on which the lid sheet is wound up, said wheel having a effective winding surface which remains approximately constant when tension in the lid sheet increases. In one aspect, this is achievable by fashioning the lid driver in 'collapsible wheel' form wherein the wheel collapses (i.e. the diameter of the wheel itself decreases) as lid sheet becomes wound around it to give it an overall approximately constant effective winding diameter (as defined by the diameter of the wheel and the strip wound around it). Suitably, said 'collapsible wheel' comprises a plurality of resiliently flexible arms each extending there from at an angle with respect to a radius. The leading end of the lid sheet is looped over one of said resiliently flexible arms to secure the lid sheet to the wheel initially.

Alternatively, the lid driver comprises a wheel on which the lid sheet is wound up, said lid sheet wheel having an effective winding surface, the effective diameter of which increases after every use of the dispenser as the lid sheet winds around the wheel. Compensation means are then provided to compensate for this increase, which would otherwise lead to a variation in the tension experienced by the lid sheet over its length and hence a variation in its indexing over time.

In one aspect, the dispenser comprises compensating means positioned between said opening station and said lid sheet wheel for reducing the length of said lid sheet therebetween to compensate for any increase in the diameter of the effective winding surface of the lid sheet wheel during use of the dispenser.

In one aspect, the compensating means takes the form of a torsion spring mounted at the lid driver that provides compensating torsional force to the lid driver such that the tension provided at the lid sheet remains approximately constant over the length of the blister strip.

Suitably, the dispenser comprises a guide for guiding the lid sheet and base sheet along separate paths at the opening station. The lid sheet is passed around the guide portion onto the lid driver. In one aspect, the guide comprises a roller mechanism. The lid sheet is fed over the rollers onto the lid driver.

Suitably, the indexer comprises a rotatable index wheel having recesses therein, said index wheel being engageable with a medicament carrier in use with said medicament dispenser such that said recesses each receive a respective pocket of the base sheet of a blister strip in use with said medicament dispenser.

Suitably, the housing of the medicament dispenser additionally comprises a first chamber in which at least one medicament carrier is initially housed and from which it is dispensed and a second chamber to receive the used portion of the base sheet after it has been indexed around the index wheel and separated from the lid sheet. Suitably, said first chamber and said second chamber are separable by a wall. In one aspect, said wall is movable to adjust the size of said first and second chambers. In another aspect, the wall is pivotally mountable. Alternatively the wall is slidably mountable.

Suitably, the cover is mounted to the housing by a suitable mounting such as a pivot mounting.

The movement of the cover from its first position to its second position is reversible and enables reversible covering and at least part-uncovering of the mouthpiece. Further, such reversible movement from the first to second position does not result in any actuation of the dispensing mechanism.

On moving the cover from the second to the third position, the cover couples (e.g. directly or indirectly engages) the dispensing mechanism such as to result in actuation thereof.

Preferably, the movement of the cover from first to second to third positions is by movement along a defined path. The path may for example be linear or arcuate (e.g. about a rotational axis).

Suitably, the nature and direction of the path is defined by the form of the mounting of the cover to the housing. In one aspect, a track is defined within the housing for receipt of a track follower provided to the cover, and in following the track a suitable path is defined.

Alternatively, the cover is arranged for rotational movement about an axis. Suitably, the cover interacts with a ratchet, which in turn interacts with a drive gear for drive of the dispensing mechanism. Suitably, in the first position the ratchet is spaced from the drive gear and in the second position the ratchet engages the drive gear such that further movement thereof (e.g. to the third position) results in movement of the drive gear, and hence advancement of the dispensing mechanism.

Suitably, the ratchet and/or drive gear is provided with an anti-return feature to prevent return (i.e. reverse) rotation thereof.

Optionally, the medicament dispenser herein comprises an actuation or dose counter for counting the number of actuations of the indexer or releases of dose from the medicament dispenser. The dose counter may count the number of doses left to be taken or the number of doses taken. The dose counter may be mechanical or electronic in form.

Optionally, the medicament dispenser additionally comprises an electronic data management system. The electronic data management system has input/output capability and comprises a memory for storage of data; a microprocessor for performing operations on said data; and a transmitter for transmitting a signal relating to the data or the outcome of an operation on the data. The electronic data management system may be integral with the body of the dispenser. Alternatively, the electronic data management system forms part of a base unit that is reversibly associable with the body.

According to another aspect of the present invention there is provided the use of the dispenser herein for dispensing a medicament product.

Other aspects and features of the invention will be apparent from the following detailed description of exemplary embodiments and from the accompanying claims.

BRIEF DESCRIPTION OF THE DRAWINGS

The invention will now be described with reference to the accompanying drawings in which.

DETAILED DESCRIPTION OF THE DRAWINGS

Figure 1:
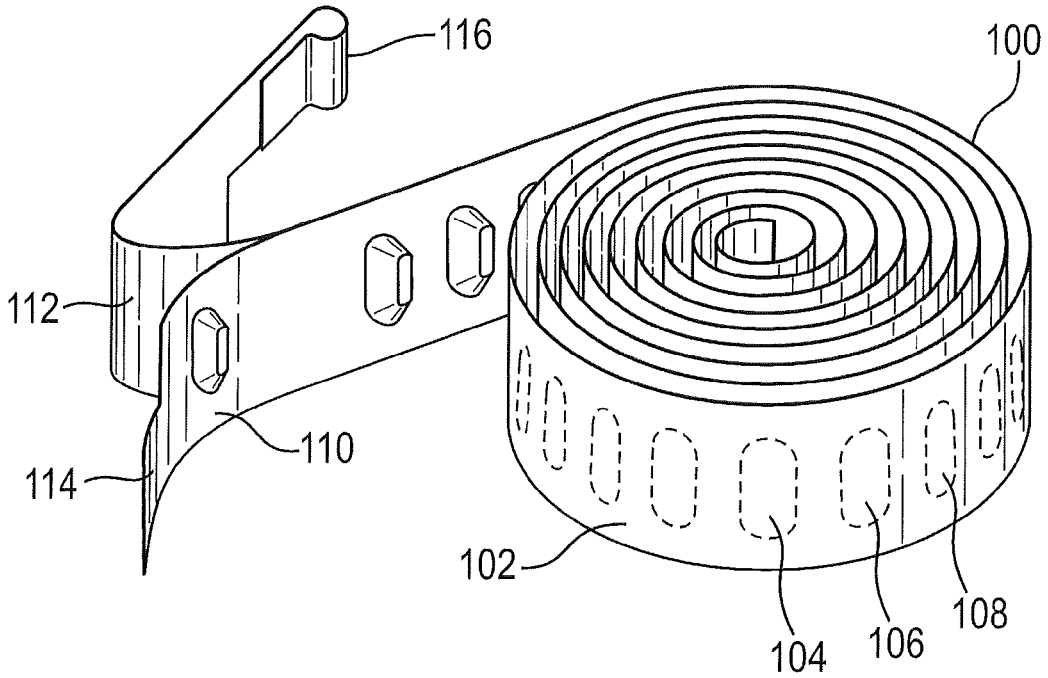
FIG. 1 shows a perspective view of a medicament carrier suitable for use in accord with the medicament dispenser of the present invention.

FIG. 1 shows a medicament carrier 100 suitable for use in accord with the present invention, which carrier 100 is of the type used in the DISKUS® ADVAIR®) inhaler of GlaxoSmithKline.

The medicament carrier comprises a flexible strip 102 defining a plurality of pockets 104, 106, 108 each of which contains a portion of a dose of medicament of a form suitable for inhalation and in the form of powder. In accord with the present invention, plural such strips 102 are typically employed in a single medicament dispenser, wherein each strip provides the component medicament dose portions of a combination medicament product. Each strip may be of the same size and/or contain the same dose amount (e.g. volume or mass) or in alternative embodiments, strips of different sizes and/or containing different dose amounts may be employed in combination.

The strip comprises a base sheet 110 in which blisters are formed to define the pockets 104, 106, 108 and a lid sheet 112 which is hermetically sealed to the base sheet except in the region of the blisters in such a manner that the lid sheet 112 and the base sheet 110 can be peeled apart. The sheets 110, 112 are sealed to one another over their whole width except for the leading end portions 114, 116 where they are preferably not sealed to one another at all.

The lid 112 and base 110 sheets are each formed of a plastics/aluminium laminate and are suitably adhered to one another by heat sealing. The lid sheet 112 comprises at least the following successive layers: (a) paper; adhesively bonded to (b) polyester; adhesively bonded to (c) aluminium foil; that is coated with a heat seal lacquer for bonding to the base sheet. The base sheet 110 comprises at least the following successive layers: (a) oriented polyamide (OPA); adhesively bonded to (b) aluminium foil; adhesively bonded to (c) a third layer comprising a polymeric material (e.g. polyvinyl chloride).

The strip 102 is shown as having elongate pockets 104, 106, 108 which run transversely with respect to the length of the strip 102. This is convenient in that it enables a large number of pockets 104, 106, 108 to be provided in series arrangement along a given strip 102 length. The strip 102 may, for example, be provided with sixty or one hundred pockets but it will be understood that the strip 102 may have any suitable number of pockets.

In a preferred embodiment of the first and second medicament dispensers in accordance with the present invention hereinafter to be described with reference to FIGS. 2 to 13, the dispensers contain two identical flexible strips 102, the pockets 104,106, 108 of which strips are of the same shape and size and equi-spaced along the strip length. The pockets of each strip contain the same medicament powder therein, the amount (dose portion) in each pocket of the strip being the same as in the other pockets of that strip. However, one strip will have at least one different active ingredient in its medicament powder than the other strip. Thus, in use the patient is able to simultaneously inhale one dose portion from each strip, the combined dose portions constituting a multi-active fixed dose therapy.

FIGS. 2a to 2e show sequential steps for preparing a hand-held, hand-operable medicament dispenser herein for use, the dispenser in this particular embodiment being a dry powder inhaler (DPI). For simplicity, only parts referred to in the corresponding description below are labelled on each Figure.

Figure 2A:
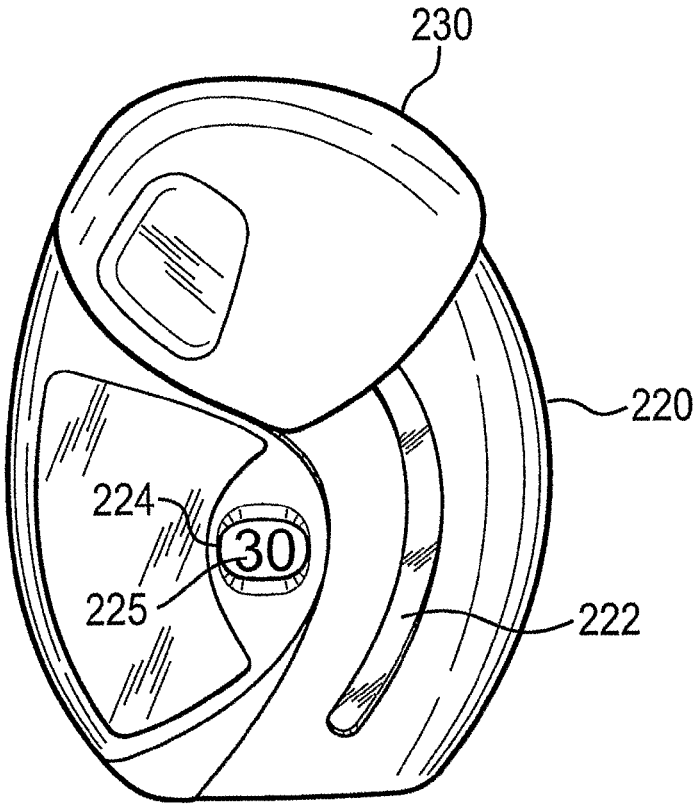
FIGS. 2a to 2e show in perspective view sequential steps for preparing a first medicament dispenser herein for use.

FIG. 2a shows the medicament dispenser comprising a housing 220, in which track 222 is defined for receipt of follower (not visible) provided to mouthpiece cover 230. In use, the mouthpiece cover 230 is movable along a path defined by the relation between the follower and track 222. In FIG. 2a, the mouthpiece cover 230 is in a first position in which mouthpiece is not visible. In other words, the mouthpiece is covered and protected by the cover 230. Also provided to housing 220 is window 224 through which a dose count indicia 225 is visible, in this instance of '30'.

Figure 2B:
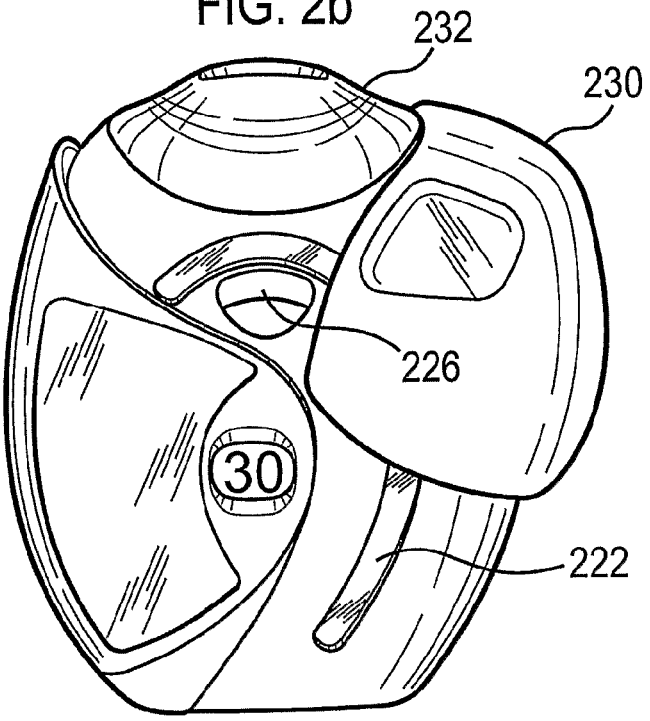

In FIG. 2b, the mouthpiece cover 230 has been moved to a second position, in which mouthpiece 232 is uncovered. Also now visible is part of snap-fit lock 226, which interacts with a similar feature (not visible) on the mouthpiece cover 230 to lock the cover 230 in place when in the first position of FIG. 2a. Movement of the cover 230 from the first position to the second position does not actuate a dispensing mechanism (not shown) in the dispenser nor actuation of the dose counter (mechanism not shown).

Figure 2C:
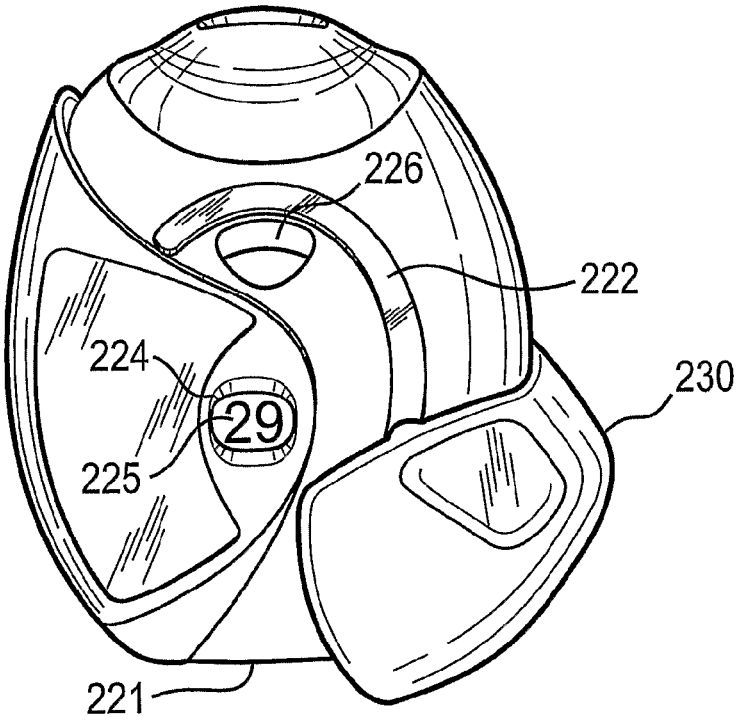

In FIG. 2c, the mouthpiece cover 230 has been moved further along the track 222 to a third position, in which part of the cover 230 extends beyond the base 221 of the housing. As a result of the further movement from the second to third position the dispensing mechanism (not visible) is actuated in the dispenser to make a medicament dose available for inhalation. In other words, the medicament dispenser is now primed for use. The movement has also resulted in actuation of the dose counter of the medicament dispenser such as to decrease the dose count indicia 225 by one unit, here to a new reading of '29'.

Figure 2D:
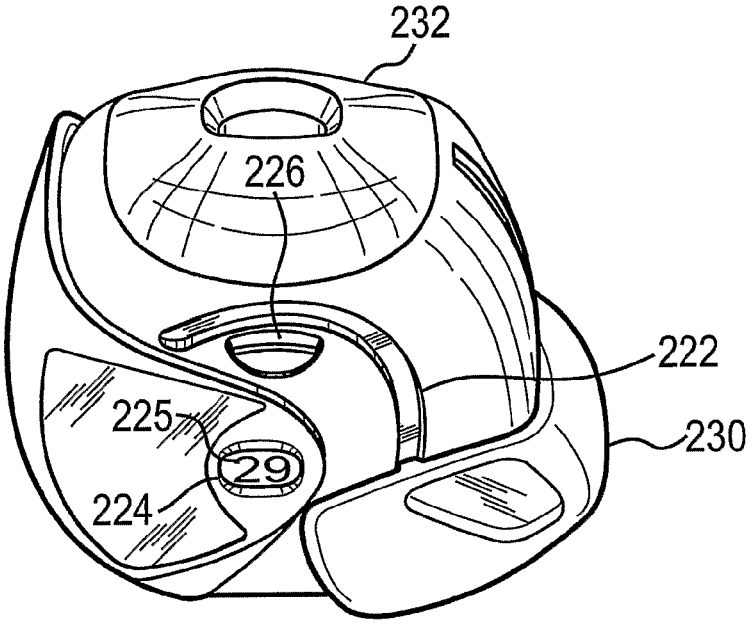
Figure 2E:
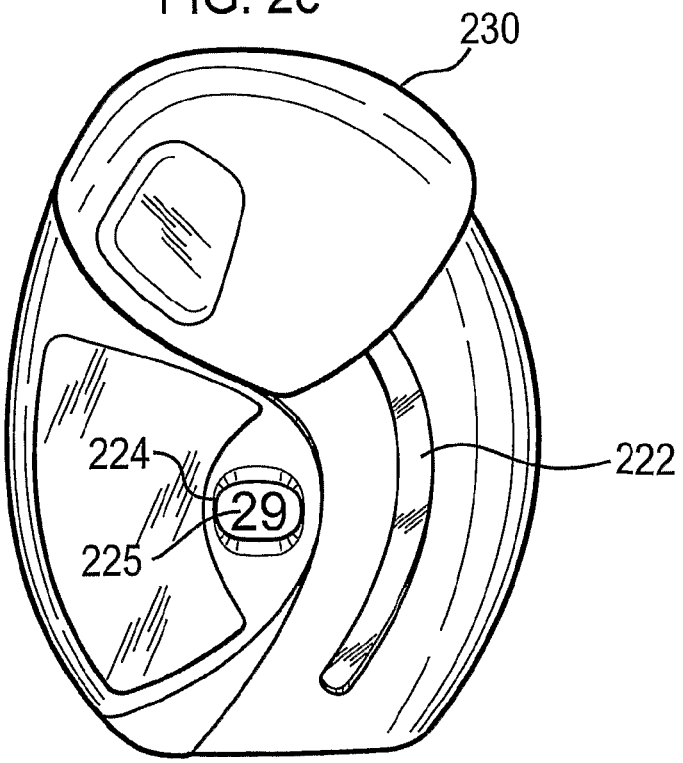

In FIG. 2d, the medicament dispenser is presented to the patient for inhalation through the mouthpiece 232.

After use, the mouthpiece cover 230 is returned to the first position (i.e. as in FIG. 2a). This corresponds to the storage ('mouthpiece protected') position of the dispenser.

It will therefore be seen that the first medicament dispenser provides for movement of the mouthpiece cover 230 to actuate the dispenser and also, in this embodiment, actuation of the dose counter. The first medicament dispenser also provides for movement of the cover 230 to a part-open position (the first position) without causing actuation of the dispenser nor, in this embodiment, actuation of the dose counter. This allows the patient to clean the mouthpiece 232 and reduces the potential for inadvertent or accidental use of the dispenser, for example by a patient playing or toying with the mouthpiece cover 230.

FIGS. 3a to 3c and FIGS. 4a to 4c each show corresponding sequential steps for preparing a second hand-held, hand-operable medicament dispenser herein for use, the dispenser in this particular embodiment again being a DPI. For simplicity, only parts referred to in the corresponding description below are labelled on each Figure.

The second medicament dispenser is of the type disclosed in US-A-2005/0154491 (Anderson et al), the entire content of which is incorporated herein by reference. That is to say, the second medicament dispenser is provided with two medicament carriers (blister strips) as shown in FIG. 1 (see FIG. 8, references 300a, 300b). A first one of the strips contains the same medicament powder in each of its pockets, with the amount of active ingredient(s) also being the same in each pocket of that strip. The other strip similarly contains a common medicament powder in each of its pockets, each pocket again having the same amount of active ingredient(s) therein. The medicament powder in each strip may contain a single active ingredient or a mixture of active ingredients. However, the medicament powder in one strip contains at least one active ingredient not in the other strip. As to be detailed further hereinafter, on operation of the second medicament dispenser, a pocket of each blister strip is peeled open to expose the different medicament powders therein. The patient then inhales on the mouthpiece (FIG. 3c, reference 332) to simultaneously inhale the powders in the open pockets of the strips 300a, 300b. The patient thus receives a fixed metered dose of medicament powder of which the different medicament powders in each pocket make up respective dose portions.

Figure 3A:
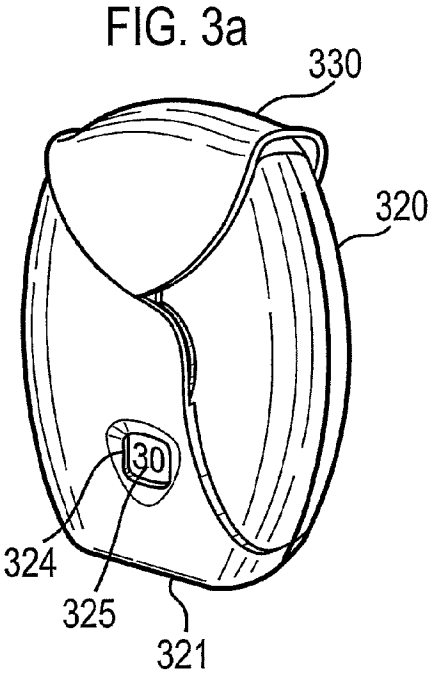
FIGS. 3a to 3c show in perspective view sequential steps for preparing a second medicament dispenser herein for use.
Figure 4A:
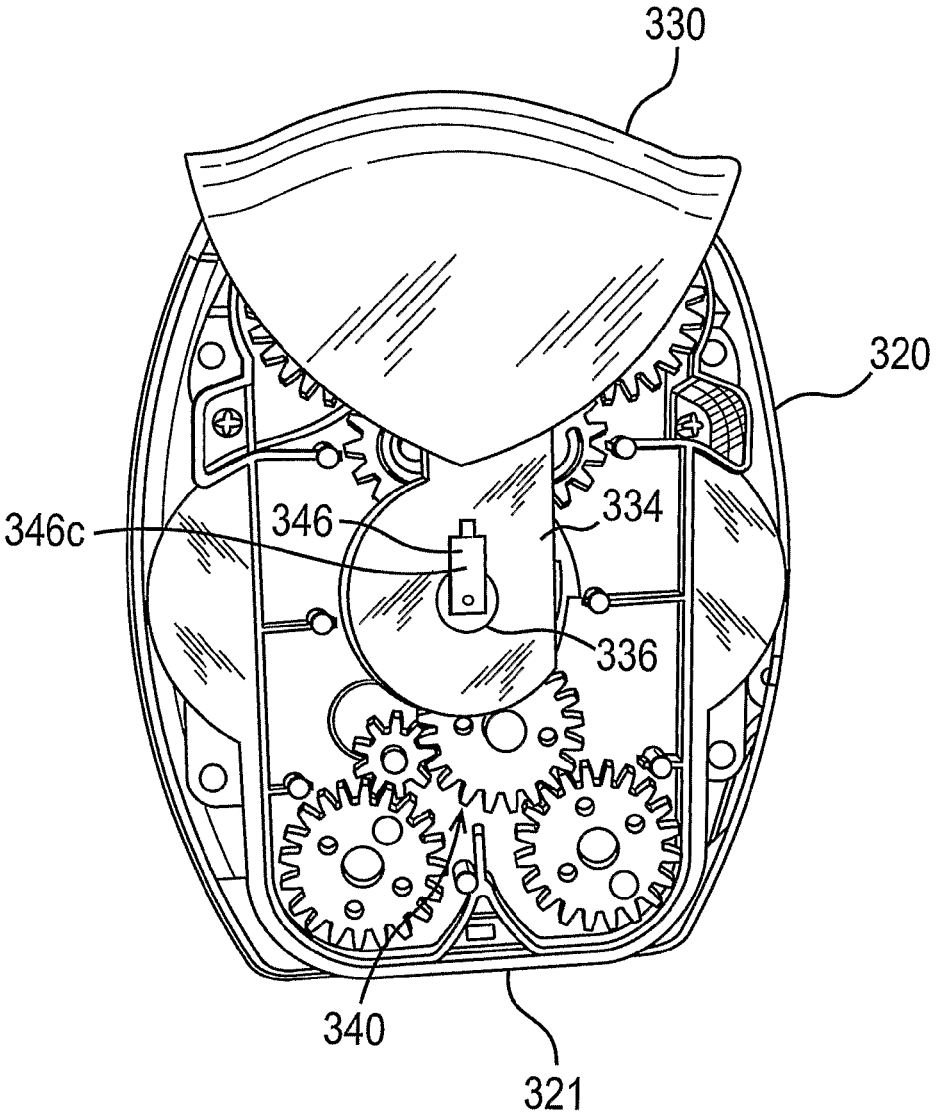
FIGS. 4a to 4c show in side view corresponding sequential steps for preparing the second medicament dispenser for use where the dispenser is shown absent its outer housing.

FIGS. 3a and 4a show a medicament dispenser comprising a housing 320 provided with a mouthpiece cover 330. As may be seen in FIG. 4a, the mouthpiece cover 330 has an arm 334 provided with a mounting aperture 336 for mounting for interaction with a ratchet 346 of a complex gear mechanism 340. In use, the mouthpiece cover 330 is rotationally movable about an axis defined by the rotational axis of the ratchet 346. In FIGS. 3a and 4a, the mouthpiece cover 330 is in a first position in which the mouthpiece is covered thereby. Also provided to housing 320 is window 324 through which a dose count indicia 325 of a dose counter (not shown) may be viewed.

Figure 3B:
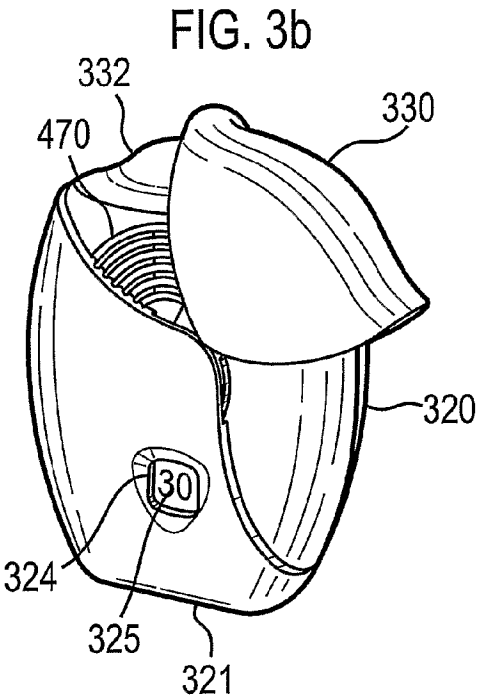
Figure 4B:
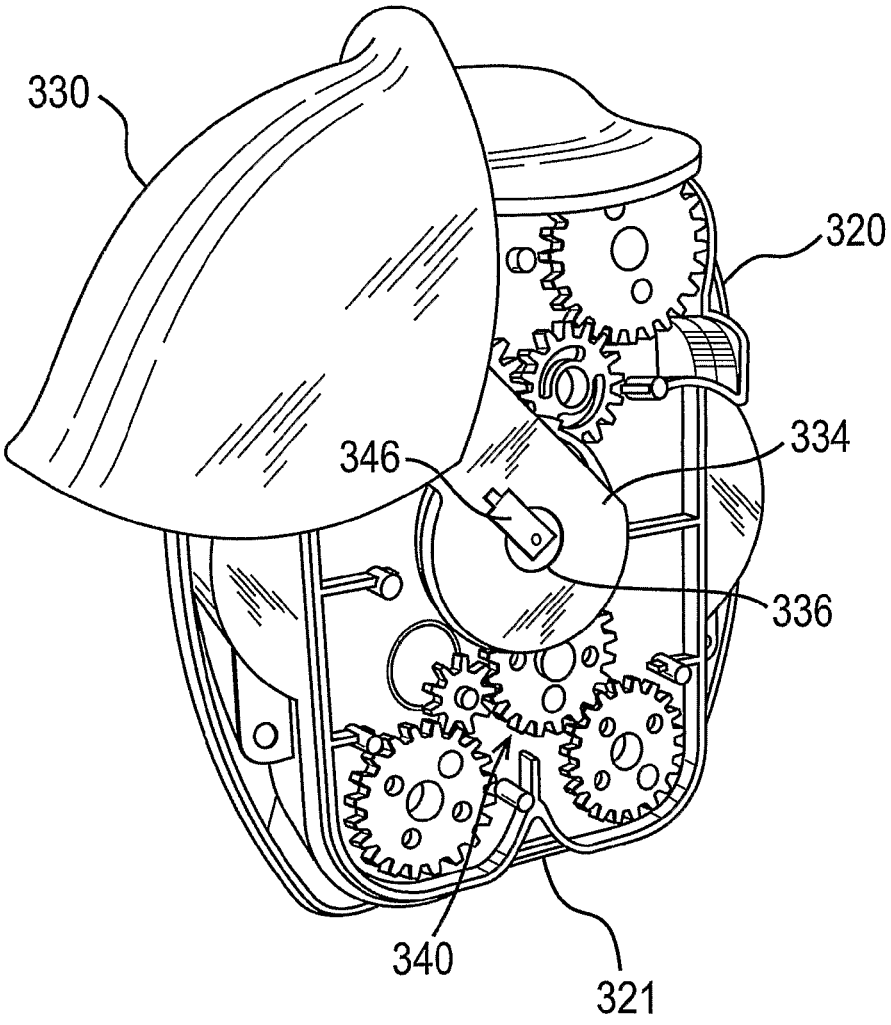

In FIGS. 3b and 4b, the mouthpiece cover 330 has been rotated to a second position, in which mouthpiece 332 is part-uncovered, but in which the gear mechanism 340 and an associated dispensing mechanism, as described in more detail below, is not actuated whereby no medicament dose is made available for inhalation. Additionally, no actuation of the dose counter (not shown) has taken place whereby the count indicia stays the same.

Figure 3C:
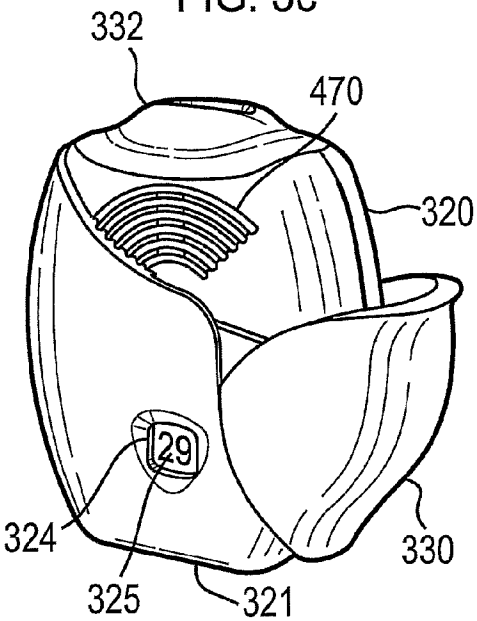
Figure 4C:
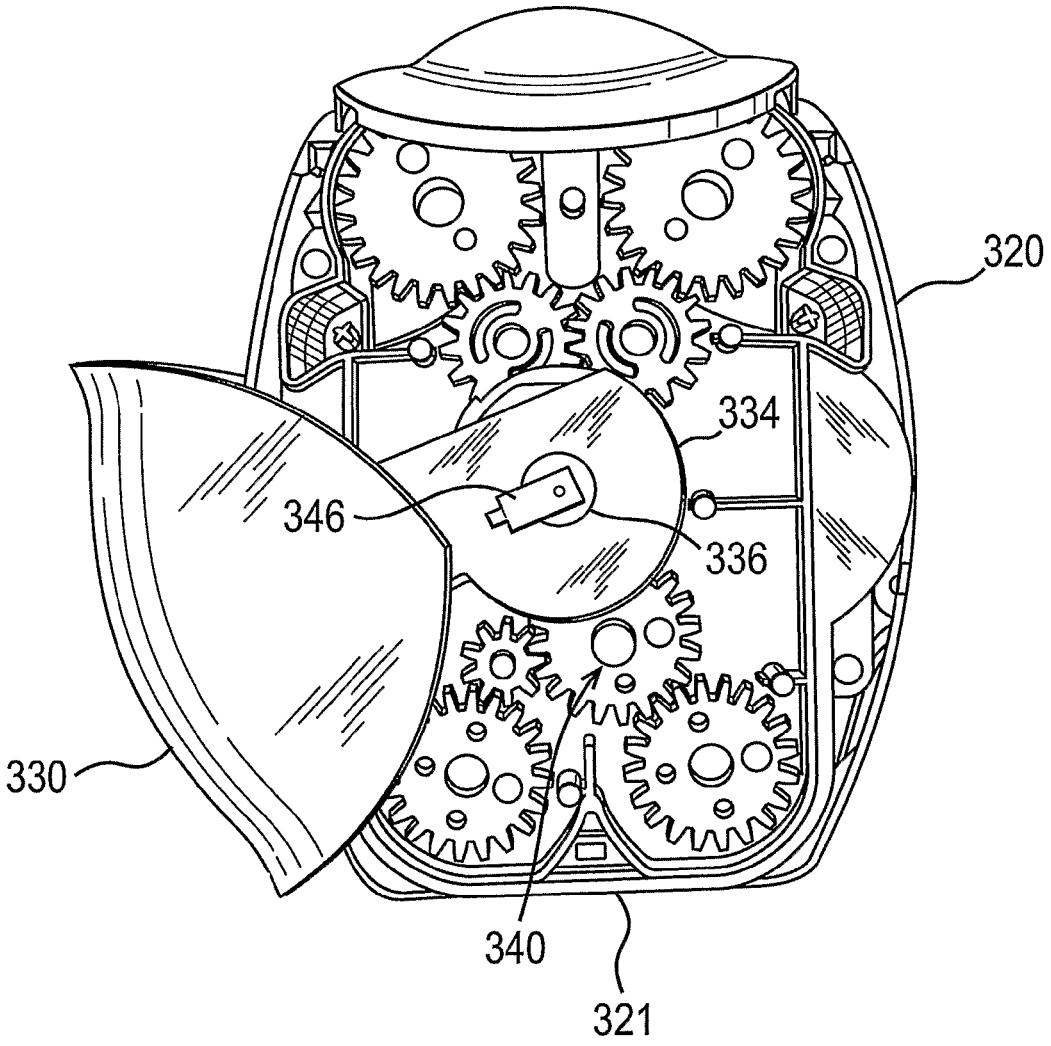

In FIGS. 3c and 4c, the mouthpiece cover 330 has been rotated further to a third position to fully uncover or open the mouthpiece 332. Part of the cover 330 extends almost to the base 321 of the housing 320 in this position. As a result of the further movement from the second to third position the gear mechanism (described in more detail with reference to FIGS. 5 and 6a to 6c below) and dispensing mechanism (described in more detail with reference to FIG. 8 below) have been actuated in the dispenser to make a medicament dose available for inhalation. In other words, the medicament dispenser is now primed for use. The movement has also resulted in actuation of the dose counter (mechanism not visible) of the medicament dispenser such as to decrease the dose count indicia 325 by one unit to a new reading of '29'.

After use, the mouthpiece cover 330 is returned to the first position (i.e. as in FIGS. 3a and 4a). This corresponds to the storage ('mouthpiece protected') position of the dispenser.

Figure 5:
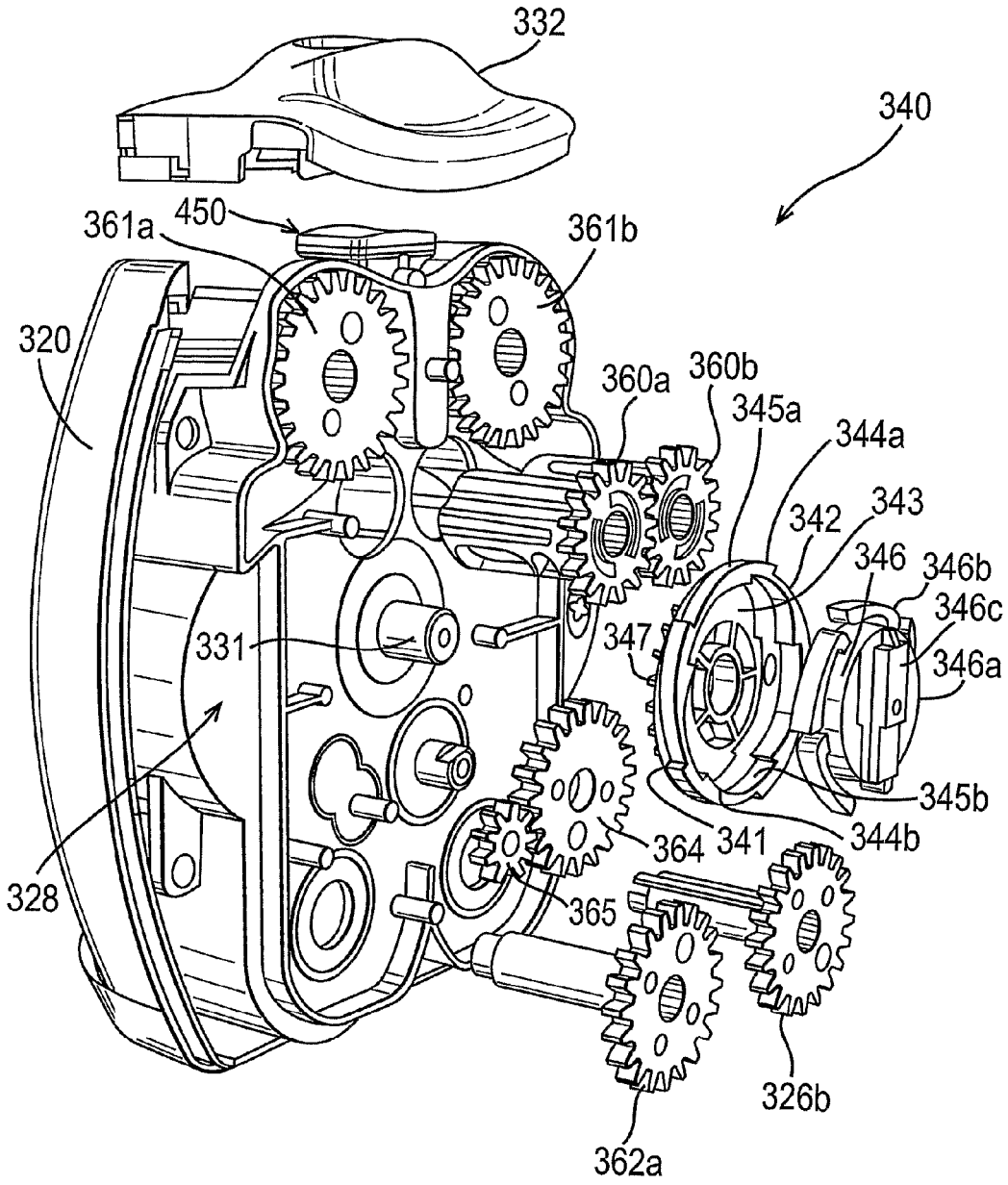
FIG. 5 shows in exploded perspective view the gear mechanism of the second medicament dispenser.

Referring now to FIG. 5, the housing 320 may be seen to be provided with the mouthpiece 332, which interacts with a manifold 450 that is arranged in use, to direct medicament powder from the opened pockets of each medicament carrier 300a, 300b at an opening station 327 (see FIG. 8) for inhalation by a patient.

FIG. 5 also shows aspects of the gear mechanism 340 of the second medicament dispenser herein. Housing 320 may be seen to be provided with an internal chassis 328 for outward receipt of the parts of the gear mechanism 340. Within the chassis 328, and as better seen by reference to FIG. 8, there are provided mirror-image (left and right) dispensing mechanisms 350a, 350b for dispensing medicament. The gear mechanism 340 can be considered to form part of the dispensing mechanisms 350a, 350b.

Figure 8:
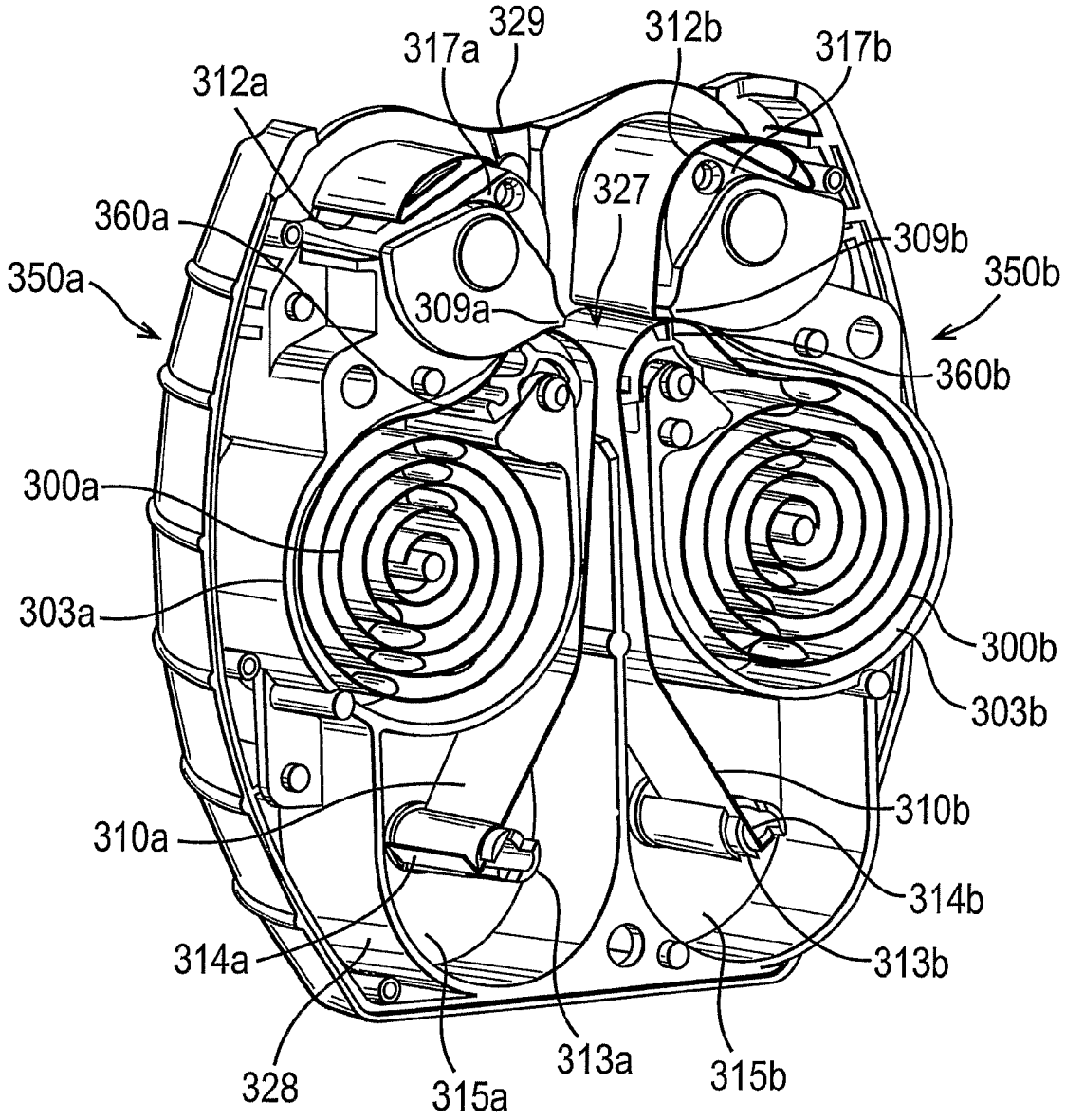
FIG. 8 shows in side view the dispensing mechanism and medicament carriers of the second medicament dispenser.

Referring to FIG. 8 in more detail, first and second medicament-containing blister strips 300a, 300b are positioned within respective left and right chambers 303a, 303b of the chassis 328. Each blister strip 300a, 300b engages in respective multi-pocket index wheel 360a, 360b, of the type used in the DISKUS® inhaler of GlaxoSmithKline, as described and shown in US-A-2005/0126568 (Davies et al)—see FIG. 16, index wheel 416—and in the 'twin strip' inhalation devices of US-A-2005/0154491 (Anderson et al), and successive pockets are thereby guided towards a central opening station 327. At the opening station 327, the lid foil 312a, 312b and base foil 314a, 314b parts of each strip 300a, 300b are peelably separable about beaks 309a, 309b. The resulting empty base foil 314a, 314b coils up in respective base take-up chambers 315a, 315b. Rotatable base take-up spindle 313a, 313b anchors the end of each respective base foil 314a, 314b in its chamber 315a, 315b. Progressive rotation of each respective base take-up spindle 313a, 313b results in the 'waste' base foil 314a, 314b being wound up therearound into a tight coil. Typically, the rotation of each base spindle 313a, 313b is coupled to that of the respective index wheel 360a, 360b.

The used lid foil 312a, 312b feeds over its respective beak 309a, 309b and coils about respective lid take-up wheel 317a, 317b, which also rotate to wind up lid foil 312a, 312b thereon. Each lid take-up wheel-317a, 317b comprises a central hub, to which the lid foil 312a, 312b is attached and about which it is wound up, a central spindle (not shown) about which the hub is rotatable and on which is mounted a torsion spring (not visible). This is described in detail in WO-A-2006/018261 (Glaxo Group Limited), in particular the embodiment therein described with reference to FIGS. 1 to 4, which International application, along with the US national phase patent application derived therefrom, is incorporated herein by reference. The function of the torsion spring is to ensure a roughly constant driving tension is provided to each strip 300a, 300b by its lid take-up wheel 317a, 317b over the course of each entire strip length. In particular, each torsion spring acts to compensate for the variation in drive tension associated with the increase in the effective winding diameter of each lid take-up wheel 317a, 317b as used lid foil 312a, 312b gradually becomes wrapped therearound. Thus, uniform indexing of each strip 300a, 300b may be maintained over the entire strip length.

In use, the dispenser is primed as shown in FIGS. 3a to 3c and 4a to 4c by movement of the cover 330 from the second position (as shown in FIGS. 3b and 4b) to the third position (as shown in FIGS. 3c and 4c) to drivably rotate the index wheels 360a, 360b and lid take-up wheels 317a, 317b to advance each blister strip 300a, 300b, thereby causing the leading pocket thereof to be peeled open. To access the contents of the opened pockets, the patient then breathes in through the mouthpiece 332. This results in negative pressure being transmitted through the manifold 450 to the opened leading pocket of each strip 300a, 300b at the opening station 327. This in turn, results in the medicament powder contained within each of the opened pockets simultaneously being drawn out through the common manifold 450 to the mouthpiece 332 and hence to the patient as an inhaled combination medicament dose. This will be described in more detail later with reference to FIGS. 9 to 13.

Referring again to FIG. 5, the gear mechanism 340 may be seen to comprise ratchet gear 342 mounted on drive spindle 331. The ratchet gear 342, like the other gears, is a wheel form having opposed inner and outer faces 341, 343 (relative to the exterior of the dispenser) and an outer circumferential surface 345a therebetween. The outer face 343 is recessed to define an inner circumferential surface 345b in opposed relation to the outer circumferential surface 345a. As will be seen, the outer and inner circumferential surfaces 345a, 345b are provided with a stepped profile to give respective outer and inner ratchet features 344a, 344b for ratcheted interaction with a ratchet 346, which interaction will be described in more detail with reference to FIGS. 6a to 6c. The ratchet features 344a, 344b are equi-angularly spaced-apart ratchet teeth; in this embodiment there are 5 teeth on each circumferential surface 345a, 345b. The teeth 344a on the outer circumferential surface 345a (the 'outer teeth 344a') are offset from the teeth 344b on the inner circumferential surface 345b (the 'inner teeth 344b'). In other words, none of the inner teeth 344b lie on the same radius from the axis of rotation of the gear 342 as the outer teeth 344a.

Figure 6A:
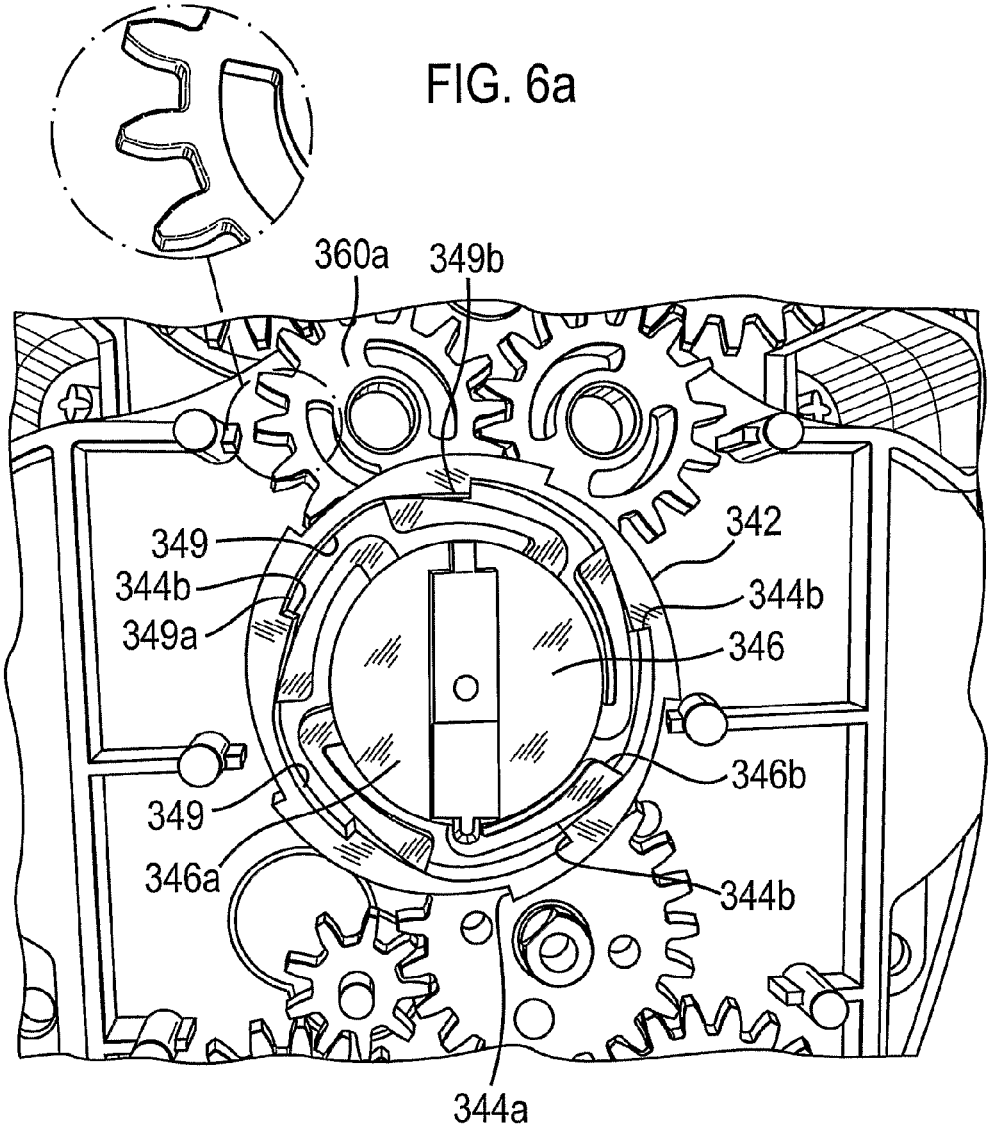
FIGS. 6a to 6c show in side view details of the gear mechanism when prepared for use in sequential steps corresponding to those of FIGS. 3a to 3c and 4a to 4c.

As will be seen from FIG. 6a, the inner circumferential surface 345b comprises surface segments 349 connecting each adjacent pair of inner teeth 344b. Each surface segment 349 consists of first and second sections 349a, 349b which extend inwardly from opposed ends of the segment 349, the first section 349a extending inwardly to the second section 349b from one inner tooth 344b and the second section 349b extending inwardly to the first section 349a from the next adjacent inner tooth 344b. The radius of curvature of the first section 349a is greater than the second section 349b whereby the second section 349b forms a ramp section with respect to the first section 349a.

Referring to FIG. 5, it will be appreciated that the base take-up spindles 313a, 313b and the spindles (not shown) of the lid take-up wheels 317a, 317b are respectively connected to base take-up gears 362a, 362b and lid take-up gears 361a, 361b. The index wheels 360a, 360b are also provided with gears. The inner face 341 of the ratchet gear 342 is provided with drive gear teeth 347 for drive interaction (meshing) with (i) the gear of a first one of the index wheels 360a, and (ii) a first idler gear 364. The gear of the first index wheel 360a meshes with a first one of the lid take-up wheel gears 361a and the gear of the second index wheel 361b, which in turn meshes with the second lid take-up gear 361b. The first idler gear 364 meshes with a first one of the base take-up spindle gears 362b and a second idler gear 365, which in turn meshes with the second base take-up spindle gear 362a. This gear train arrangement provides for indexing of the medicament carriers 300a, 300b and winding on of the base and lid sheets 310a,b, 312a,b on movement of the mouthpiece cover 330 from its second position to its third position.

A more detailed description of a suitable counter mechanism for use in the dispenser is provided in WO-A-2005/079727 (Glaxo Group Limited) which, along with the US national phase patent application derived therefrom, is incorporated herein by reference. The base take-up spindle 313b can be used to drive this counter mechanism by engagement with the drive wheel/step-up gear wheel thereof.

Figure 6B:
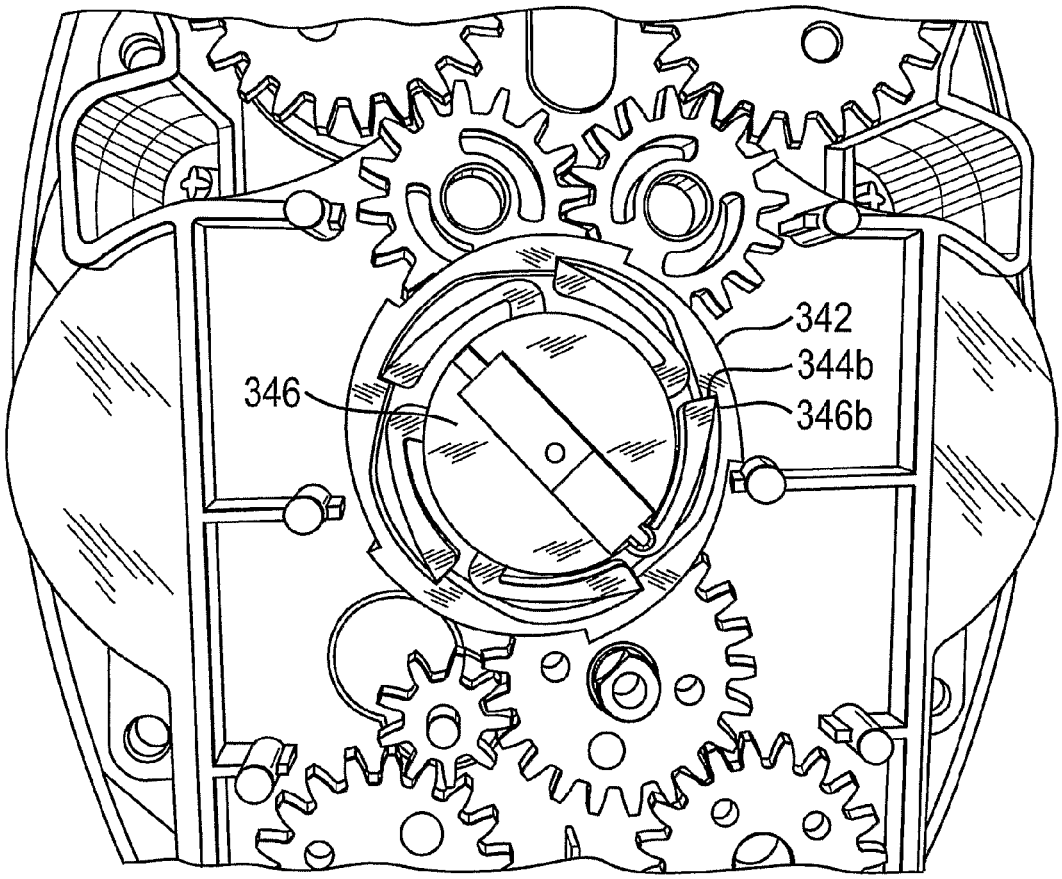
Figure 6C:
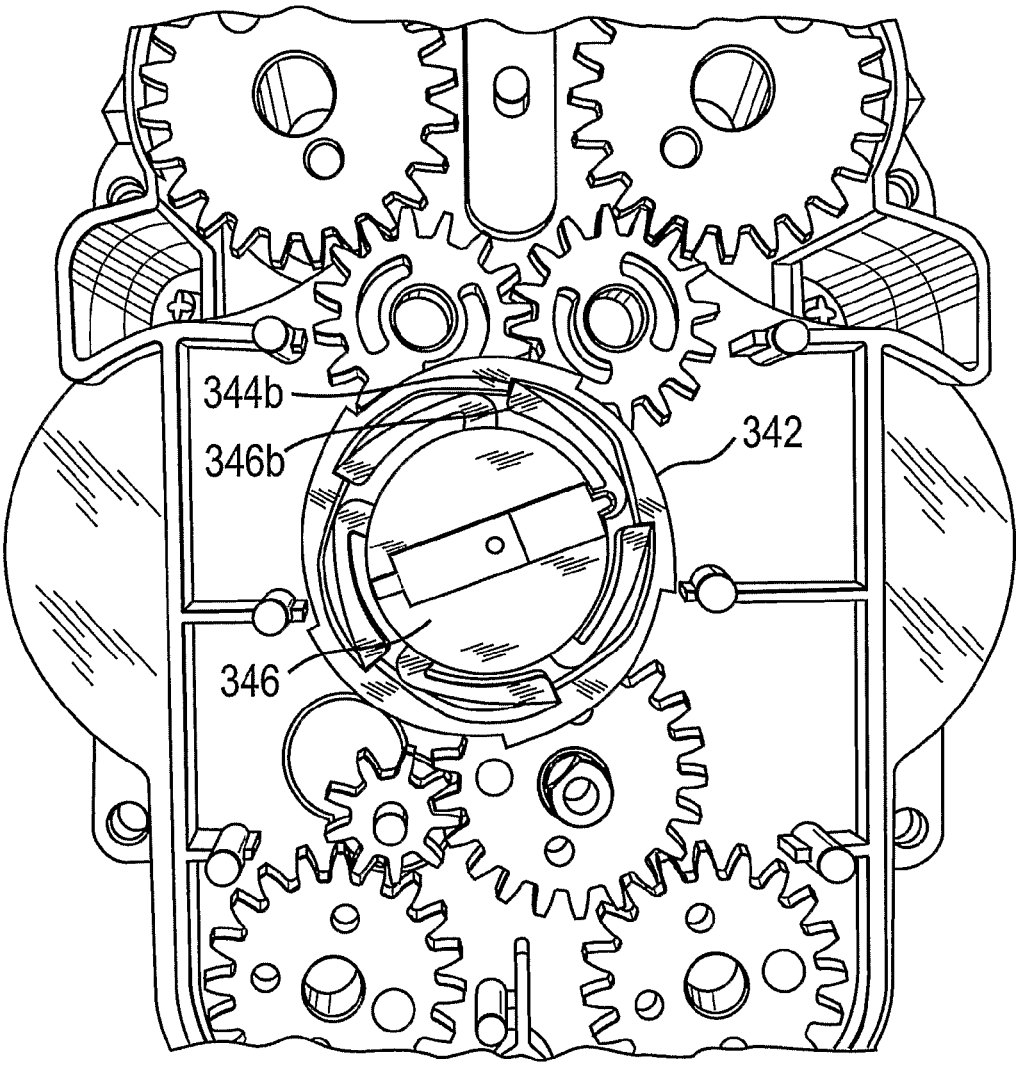
Figure 7:
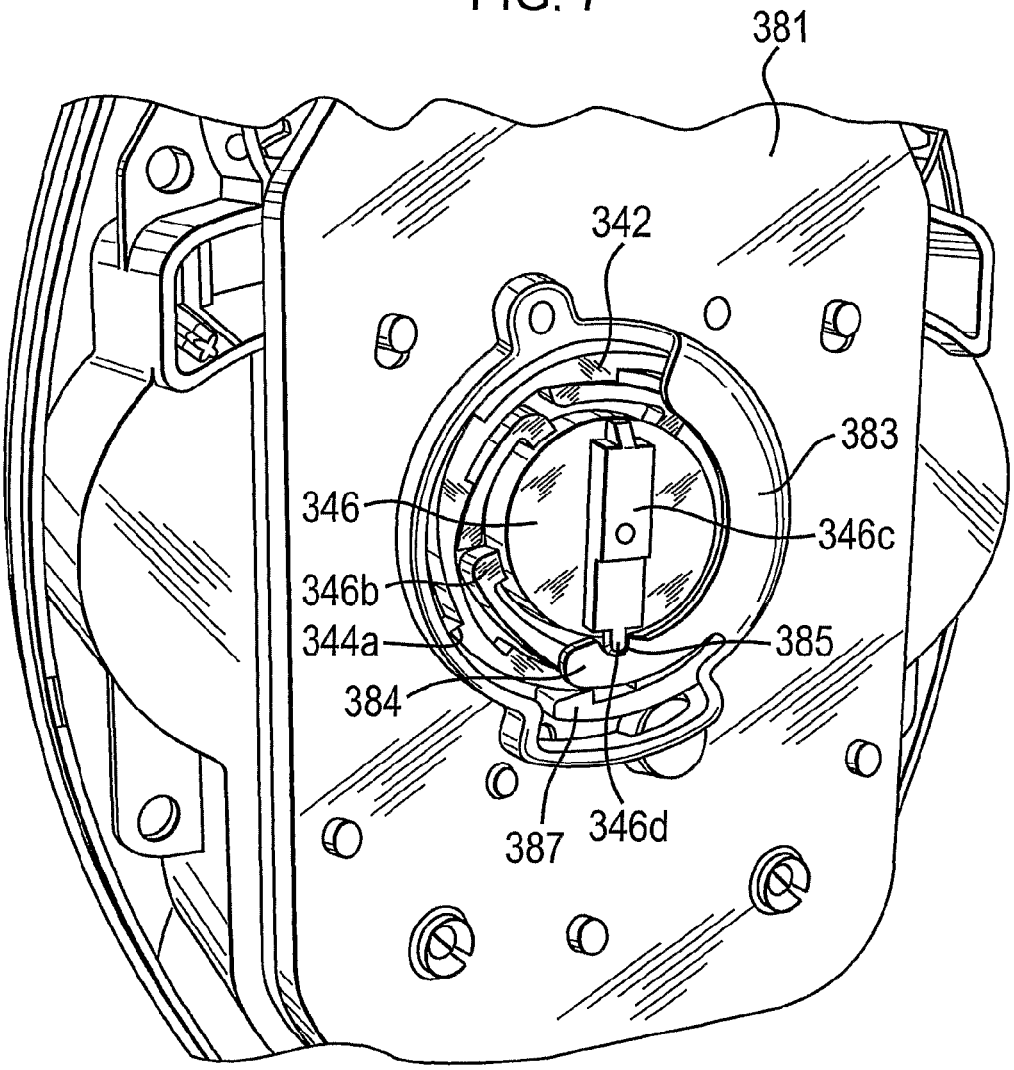
FIG. 7 shows in side view a detail of the ratchet 'anti return' mechanism of the second medicament dispenser.

As shown in FIGS. 5 to 7, the ratchet 346 comprises a central hub 346a from the outer circumference of which depend a plurality of equi-angularly spaced-apart, circumferentially-oriented, resilient legs 346b. The ratchet hub 346a further comprises a boss 346c which, as shown in FIG. 4a, fits in the mounting aperture 336 of the mouthpiece cover arm 334 for establishing a direct drive connection between the mouthpiece cover 330 and the ratchet 346 whereby rotary movement of the mouthpiece cover 330 between its first to third positions causes rotary movement of the ratchet 346 in the ratchet gear 342, as will be described in more detail shortly hereinafter. In this particular embodiment, 5 ratchet legs 346b depend from the ratchet hub 346a. In other words, the number of ratchet legs 346b is chosen to match the number of inner teeth 344b of the ratchet gear 342.

Interaction of the ratchet gear 342 with ratchet 346 may be better understood with reference to FIGS. 6a to 6c, which show movement of parts of the gear mechanism 340 of the second medicament dispenser when prepared for use in sequential steps corresponding to those of FIGS. 3a to 3c.

In the rest position of FIG. 6a (i.e. mouthpiece cover 330 closed), the ratchet 346 is angularly disposed in the ratchet gear 342 so that the inner teeth 344b of ratchet gear 342 are circumferentially spaced from the free ends of the ratchet legs 346b. In the second position of FIG. 6b (i.e. mouthpiece cover 330 partially opened), the ratchet 346 has rotated round in the ratchet gear 342 to slide the ratchet legs 346b over the adjacent surface segments 349 of the inner circumferential surface 345b to engage the inner teeth 344b. It will therefore be appreciated that in this second position, the ratchet gear 342 is ready for movement but has not yet been moved, and hence that the overall gear mechanism 340 and dispensing mechanisms 350a, 350b have not been advanced. In the third position of FIG. 6c (i.e. mouthpiece cover 330 fully opened), both the ratchet 346 and ratchet gear 342 rotate together (by 72° as shown) through inter-engagement of the ratchet legs 346b and the inner teeth 344b such as to advance the overall gear mechanism 340 and dispensing mechanisms 350a, 350b such as to index and advance each medicament carrier 300a, 330b to open a pocket of each and to thereby make the medicament powder contained in each opened pocket available at the manifold 450 at the opening station 327 for simultaneous inhalation by the patient through the opened mouthpiece 332.

Referring to FIG. 7, the dispenser further comprises an internal retaining plate 381 for covering the gear mechanism 340. The retaining plate 381 is provided with an arcuate shelf 383 which lies over the ratchet gear 342 and the ratchet 346. One end of the shelf 383 is configured as a resilient finger 384 in which is provided a notch 385. The ratchet 346 includes a protrusion 346d which engages in the notch when the ratchet (and hence the mouthpiece cover 330) is in its first, rest position of FIG. 6a, as shown in FIG. 7. This inter-engagement of the ratchet protrusion 346d and the retaining plate notch 385 acts as a detent to detent the mouthpiece cover 330 in the 'mouthpiece closed' or rest position of FIGS. 3a, 4a, 6a and 7.

The retaining plate 381 yet further comprises a fixed, resilient pawl leg 387 for interaction with the outer teeth 344a of the ratchet gear 346 to form an 'anti-return' feature for the ratchet gear 346. When the mouthpiece cover 330 is opened, to cause rotation of the ratchet 346 and then the ratchet gear 342 once the ratchet legs 346b engage the inner teeth 344b, the pawl leg 387 is not an impediment to the rotary movement of the ratchet gear 342 as the pawl leg 387 rides over the outer teeth 344a due to their orientation and the resilience of the pawl leg 387. However, when the mouthpiece cover 330 is returned to its closed position, in turn rotating the ratchet 346 to its rest position, the ratchet gear 342 is held against return rotation by engagement of the pawl leg 387 with one of the outer teeth 344a. Accordingly, the reverse rotation of the ratchet 346 on closure of the mouthpiece cover 330 is not transmitted to the gear mechanism 340. Thus, on each occasion the mouthpiece cover 330 is fully opened and closed, the ratchet gear 342 is incremented in one rotary direction only.

When the mouthpiece cover 330 is returned to its first, covering position (FIG. 3a) to rotate the ratchet 346 in the ratchet gear 342 back to its rest position (FIG. 6a), the resilient legs 346b slide back over the inner circumferential surface 345b to be spaced behind different inner teeth 344b ready for next opening of the mouthpiece cover 330.

In FIG. 6a there is shown an enlarged view of one of the gear teeth of index wheel 360a showing the profile thereof. The gear teeth of all of the gears in the gear mechanism are provided with this profile.

A more detailed description of the manifold 450 of the second medicament dispenser now follows with reference to FIGS. 9 to 13.

Figure 9:
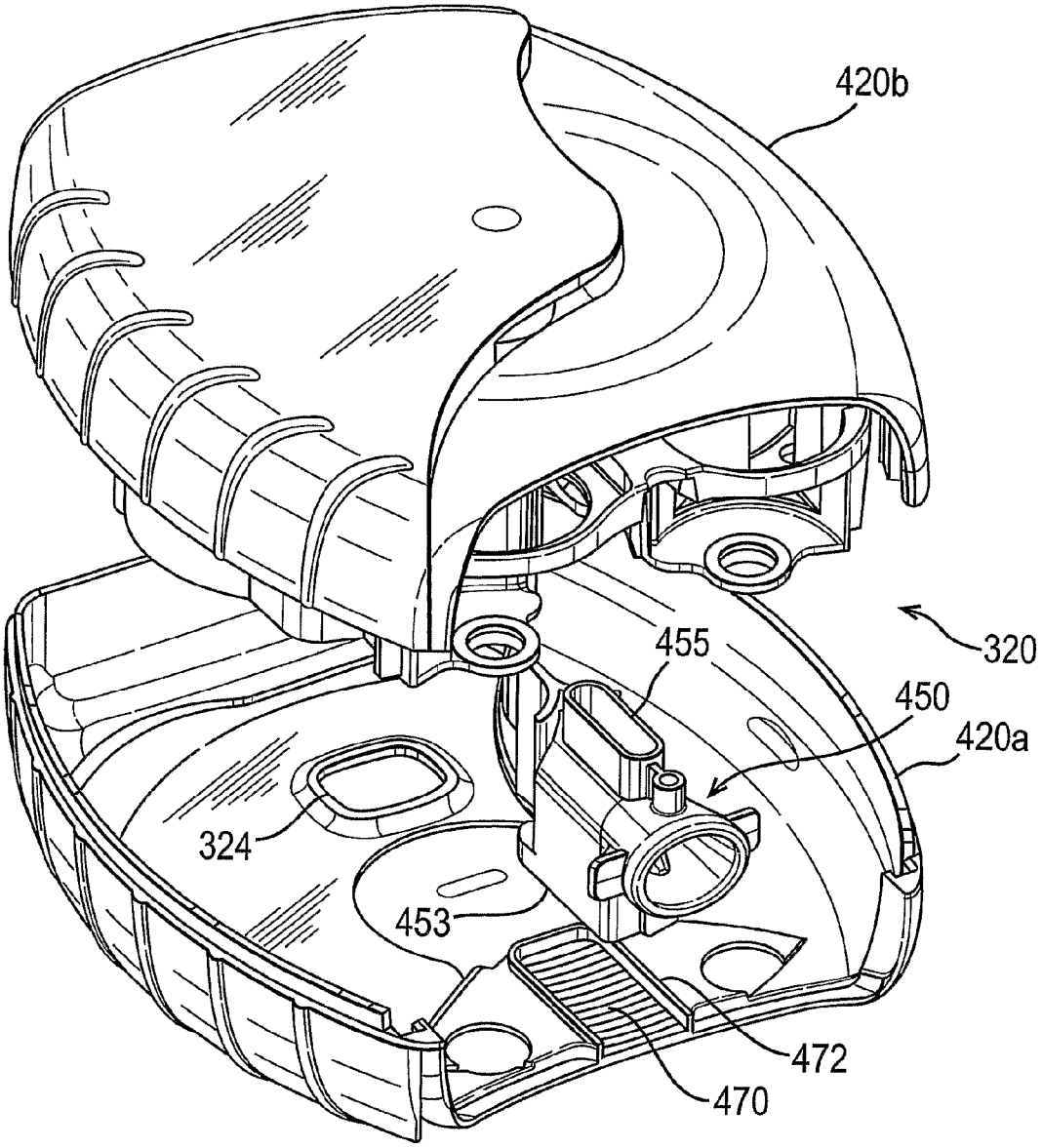
FIG. 9 shows a part-exploded view of the second medicament dispenser absent its mouthpiece.

FIG. 9 shows the second medicament dispenser absent its mouthpiece 332 and that the housing 320 comprises mating first 420a and second 420b shell cover parts. The manifold 450 is received by first shell cover part 420a such that a lip defining an inlet 453 to a manifold chimney 452 is received within an inner wall 472 of the first shell cover part 420a which defines an air inlet grille 470. The manifold 450 is also received by the second shell cover part 420b such that a protruding foot 455 of the manifold 450 sits within a manifold-receiving cavity (not shown).

As shown in FIGS. 3a-c, the air inlet grille 470 in the first shell cover part 420a is covered by the mouthpiece cover 330 when its first or closed position (FIG. 3a), part-uncovered when the mouthpiece cover 330 is in its second or part-opened position (FIG. 3b) and fully revealed when the mouthpiece cover 330 is in its third or open position (FIG. 3c).

In use, the air inlet grille 470 allows air to pass from outside the dispenser into the manifold 450 via the chimney inlet 453 to the chimney 452 in response to inhalation by the patient at the mouthpiece 332. Notably, the air inlet grille 470 provides the sole point of entry of inhalation air from outside the second medicament dispenser into its manifold 450.

Figure 10:
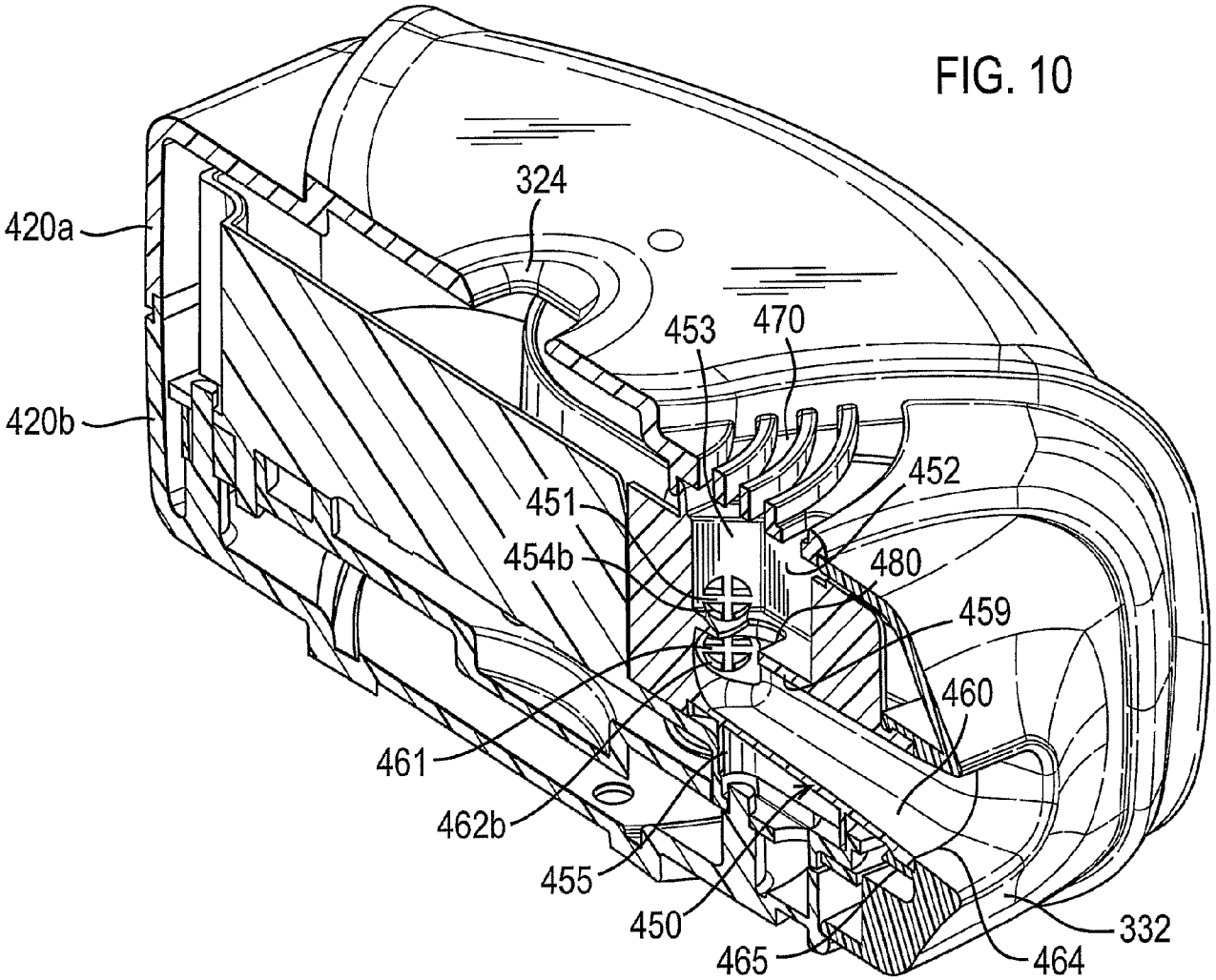
FIG. 10 shows a cut-away view of the second medicament dispenser.
Figure 11:
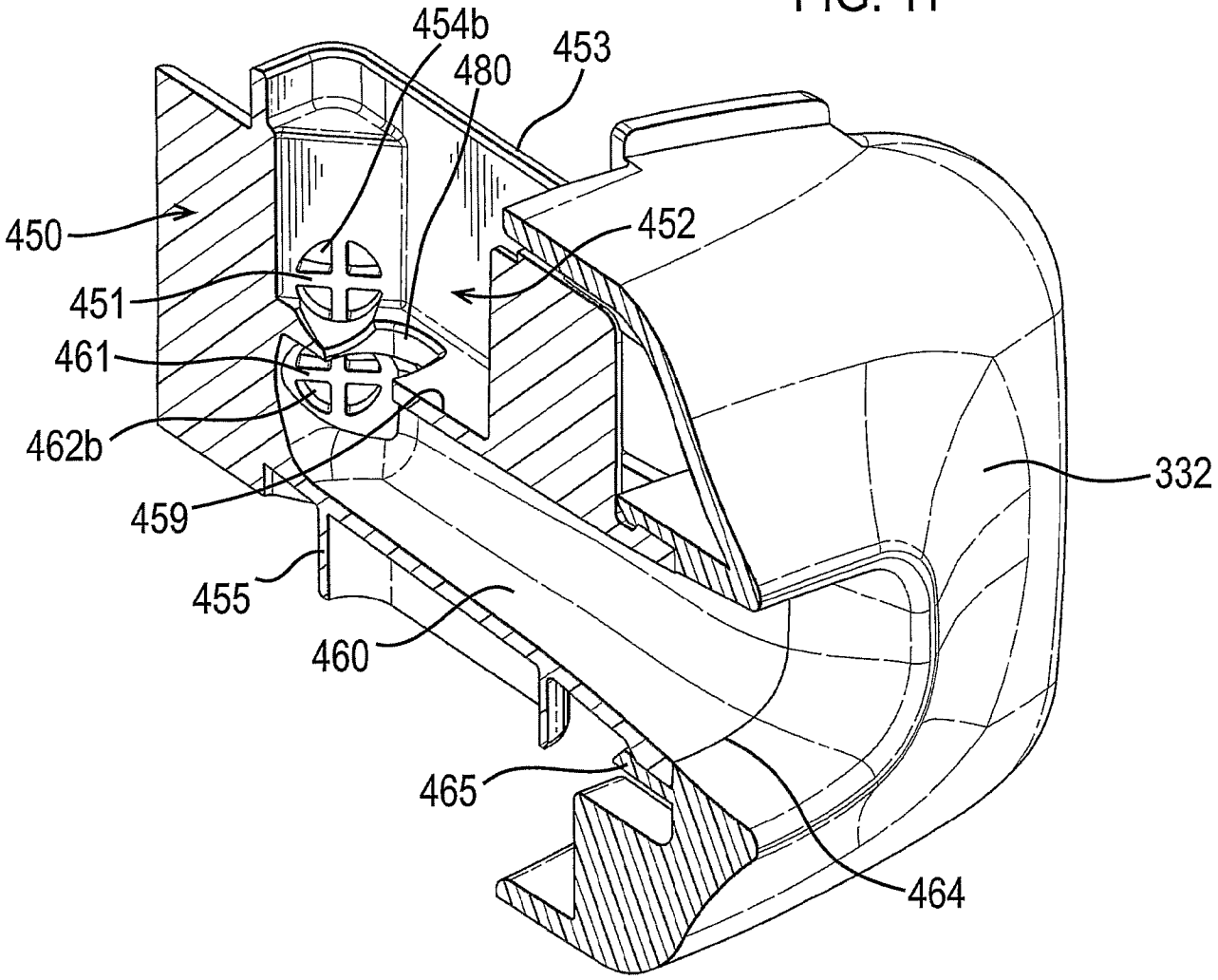
FIG. 11 shows a cut-away view of the mouthpiece and manifold assembly of the second medicament dispenser.

As may also be seen by reference to FIGS. 10 and 11, the manifold 450 has a particular inner structure in which the chimney 452 locates above a chamber 460 and partly shares a common wall 459 therewith, which common wall 459 forms the bottom (relative to illustrated orientation) wall of the chimney 452 and part of the top wall (relative to illustrated orientation) of the chamber 460.

The chimney 452 has a chimney inlet 453 and a pair of chimney exits 454a, 454b. In use, the chimney 452 directs inward airflow (as exclusively received through the air inlet grille 470 on patient inhalation) from the chimney inlet 453 to the pair of chimney exits 454a, 454b. The chamber 460 has a pair of chamber inlets 462a, 462b (only one visible) and a chamber exit 464. The pair of chimney exits 454a, 454b and pair of chamber inlets 462a, 462b are both defined by a pair of circular holes, in this particular embodiment of diameter about 3mm, and each hole is provided with a respective cruciform 451, 461. Each chimney exit 454a, 454b is paired with one of the chamber inlets 462a, 462b by positioning them adjacent to one another. The mouthpiece 332 is provided to the chamber exit 464 and snap-mounts thereto via snap-mounting feature 465.

As detailed hereinabove, when the mouthpiece cover 330 is fully opened to its third position, the gear and dispensing mechanisms are actuated to cause each blister strip 300a, 300b to be advanced and a single pocket of each strip to be peeled open. The peeled open blister pocket (not shown) of each strip 300a, 300b lies adjacent a respective one of the pairs of chimney exits 454a, 454b and chamber inlets 462a, 462b. When a patient inhales at the mouthpiece 332, an airstream flows from outside of the dispenser into the manifold 450 solely through the air inlet grille 470 into the chimney 452. First portions of this airstream flow into the opened blister pocket of each strip 300a, 300b via the respective chimney exits 454a, 454b, thereby entraining the medicament powder contained in the pockets in the airstream, and thence out of the pockets into the chamber 460 via chamber inlets 462a, 462b. The airstream with entrained medicament powder then flows out of the mouthpiece 332 into the patient's respiratory tract.

Figure 12:
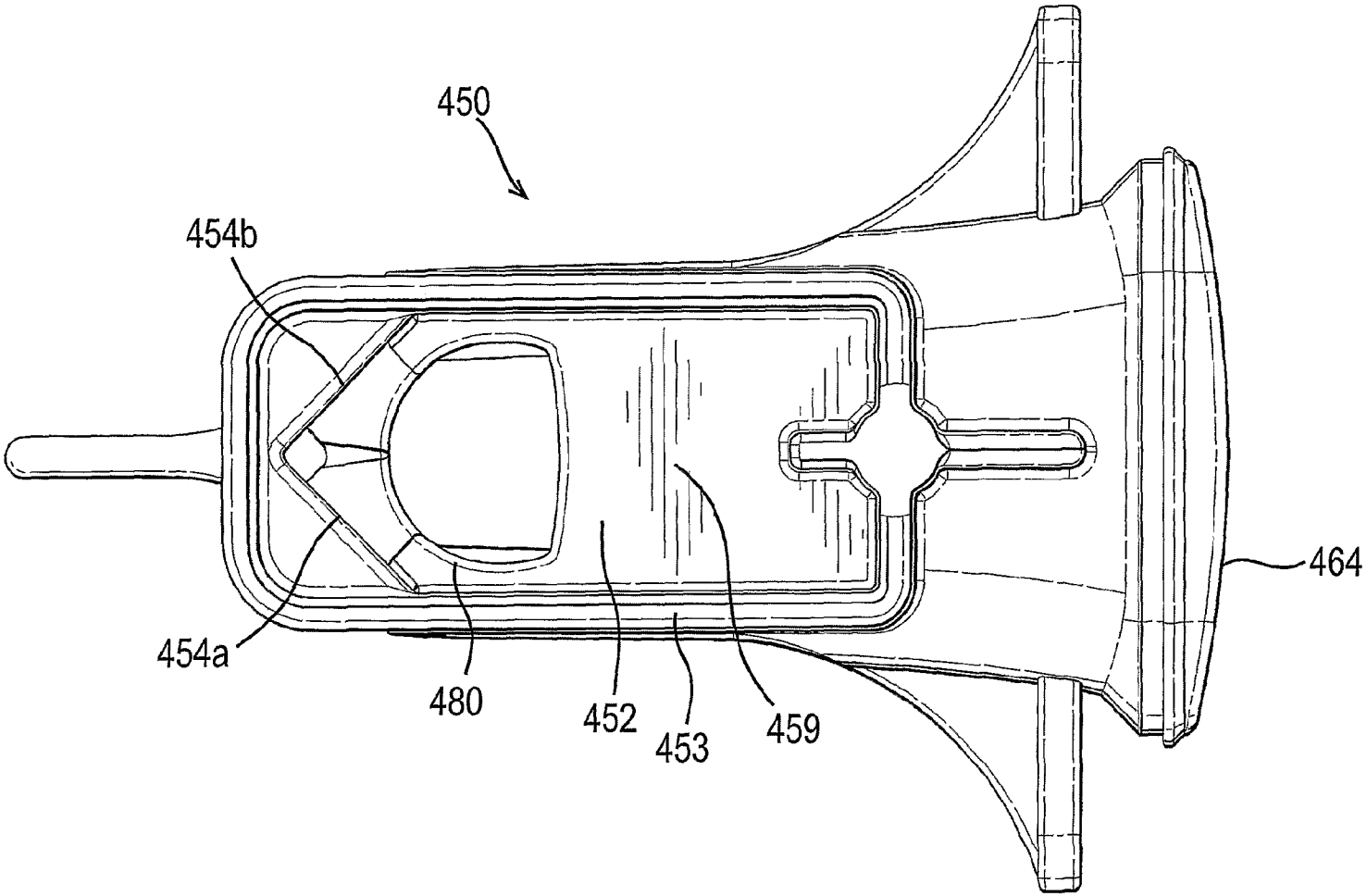
FIG. 12 shows a plan view of a first manifold for use in the mouthpiece and manifold assembly.

As shown in FIG. 12, for example, a single D-shaped bleed hole 480 is provided to the wall 459 which separates the chimney 450 from the chamber 460. The D-shaped bleed hole 480 locates adjacent to both the chimney exits 454a, 454b and the chamber inlets 462a, 462b. In use, the bleed hole 480 acts such as to direct a second portion of the airstream (the "bleed portion") from the chimney 452 into the chamber 460 to disruptively impact the first portions of the airstream that transport the entrained medicament powder into the chamber 460 and thereby break-up any powder agglomerate components thereof.

Figure 13:
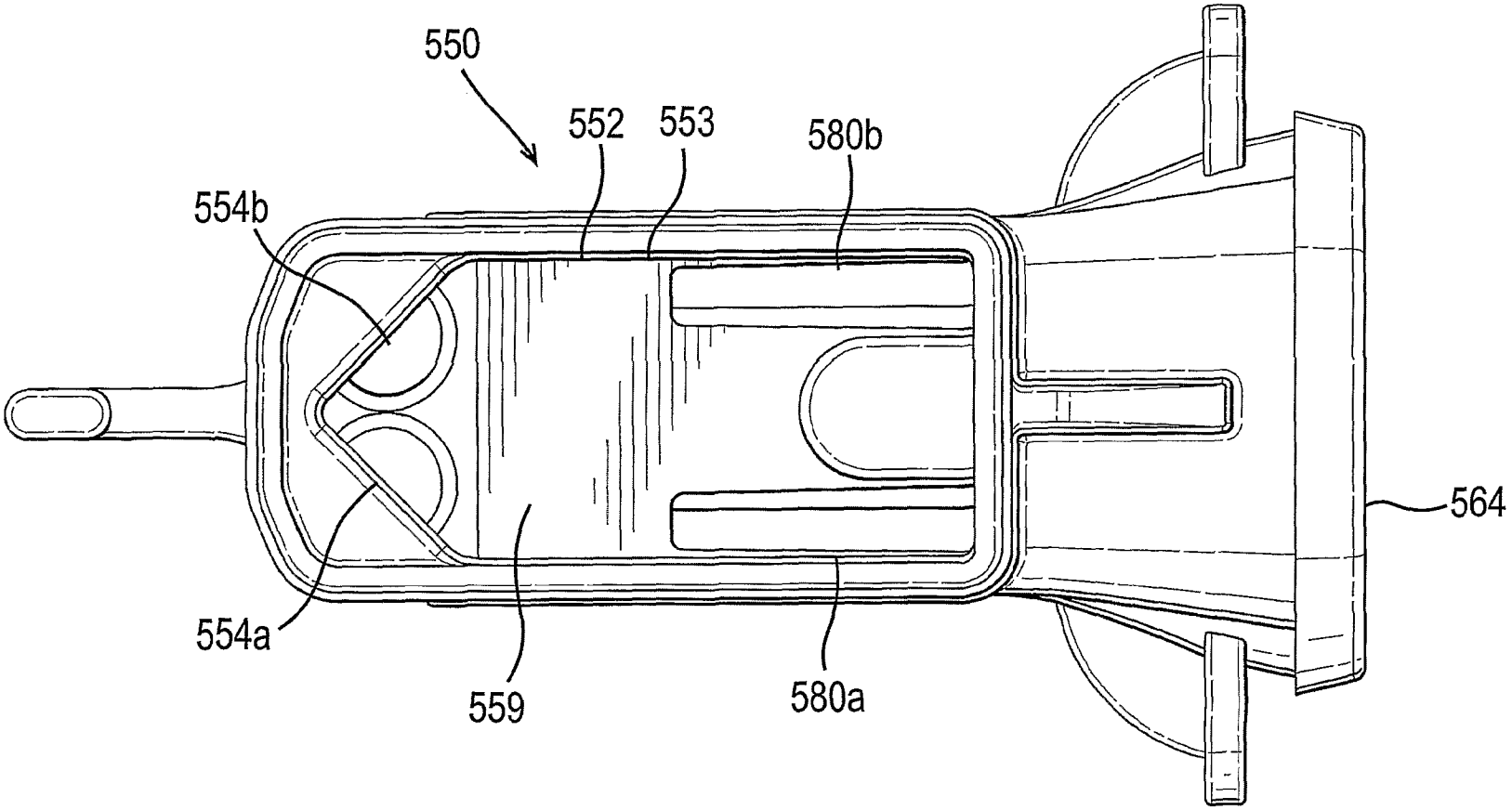
FIG. 13 shows a plan view of a second manifold for use in the mouthpiece and manifold assembly.

FIG. 13 shows a second manifold 550 that, is a variation of (and alternative to) the manifold 450 with 'D-hole' type bleed hole 480.

It will be appreciated that the overall shape and form of this second manifold 550 corresponds to that of the 'D-hole' manifold 550 such that one may be readily substituted for the other. The second manifold, however, has two elongate slot form bleed holes 580a, 580b provided to the wall 559, which separates the chimney 552 from the chamber (not visible).

In more detail, the second manifold 550 has an inner structure in which chimney 552 locates above chamber (not visible) and partly shares a wall 559 therewith, which wall 559 forms the bottom (as shown) wall of the chimney 552 and part of the top wall of the chamber (not visible).

The chimney 552 has a chimney inlet 553 and dual chimney exits 554a, 554b. In use, the chimney 552 directs inward airflow (as exclusively received through the air inlet grille 470) from the chimney inlet 553 to the chimney exits 554a, 554b. The chamber has dual chamber inlets (not visible) and a chamber exit 564. The chimney exits 554a, 554b and chamber inlets are as in the first manifold 450.

As with the first manifold 450, the chimney exits 554a, 554b and chamber inlets are adjacent to each other to form pairs against which an open blister pocket from each peelable blister strip lies so that, on patient inhalation, an airstream flows exclusively into the manifold chimney 552 via the air inlet grille 470 with first portions of the airstream being directed through the open pockets via the paired chimney exits 554a, 554b and chamber inlets to entrain the medicament powder from the open pockets into the chamber.

Elongate slot form bleed holes 580a, 580b are provided to the wall 559, which separates the chimney 552 from the chamber (not visible). The elongate slot form bleed holes 580a, 580b are located distally from both the chimney exits 554a, 554b and chamber inlets. In use, the bleed holes 580a, 580b act such as to direct a bleed portion of the airstream from the chimney 552 into the chamber to disruptively impact the medicament powder entrained into the chamber by the first airstream portions and thereby break up any powder agglomerate components thereof.

The manifold 450, 550 may be wholly or partly comprised of or alternatively coated partially or wholly with materials that reduce the tendency of medicament to adhere thereto. Such materials may, for example, raise the surface tension of the relevant manifold surface. Fluoropolymer materials may be employed. High density polyethylene (HDPE) and/or modified acetal materials are also suitable.

It will therefore be seen that the second medicament dispenser provides for movement of the mouthpiece cover 330 to actuate the dispenser and also, in this embodiment, actuation of the dose counter. The second medicament dispenser also provides for movement of the cover 330 to a part-open position (the first position) without causing actuation of the dispenser nor, in this embodiment, actuation of the dose counter. This allows the patient to clean the mouthpiece 332 and reduces the potential for inadvertent or accidental use of the dispenser, for example by a patient playing or toying with the mouthpiece cover 330.

Whilst the second medicament dispenser of FIGS. 3 to 13 has been described in relation to a dispenser comprising two medicament carriers 300a, 300b it will be appreciated that that same dispenser may be used with a single medicament carrier with one of the dispensing mechanisms not acting on any medicament carrier. Alternatively, each medicament carrier could contain the same medicament powder (i.e. same active or combination of actives).

The skilled person will appreciate that most of the components of the medicament dispenser of the invention can be made from plastics materials, e.g. as moulded plastics components, typically by injection moulding. In the second medicament dispenser of FIGS. 3 to 13, all components other than the torsion spring (which may be made from stainless steel) may be made (e.g. injection moulded) from a plastics material. In this case, all of the plastics components may be of acetal(polyoxymethylene (POM)) other than for the following plastics components:

Housing shells 420a, 420b—acrylonitrile-butadiene-styrene (ABS)

Mouthpiece cover 330—ABS

Count wheels (not shown)—ABS

Manifold 450;550—high density polyethylene (HDPE)

Counter window 324—polycarbonate (PC)

Mouthpiece 332—polypropylene (PP)

The medicament dispenser of the present invention is suitable for dispensing medicament product, particularly for the treatment of respiratory disorders such as asthma and chronic obstructive pulmonary disease (COPD), bronchitis and chest infections.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahyd ro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy) phenyl]-2-[((2S)-4-methyl-2-{[2-(2-methylphenoxy)acetyl] amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

The formulated medicament product may in aspects, be a mono-therapy (i.e. single active medicament containing) product or it may be a combination therapy (i.e. plural active medicaments containing) product.

Suitable medicaments or medicament components of a combination therapy product are typically selected from the group consisting of anti-inflammatory agents (for example a corticosteroid or an NSAID), anticholinergic agents (for example, an $M_1$, $M_2$, $M_1/M_2$ or $M_3$ receptor antagonist), other $\beta_2$-adrenoreceptor agonists, antiinfective agents (e.g. an antibiotic or an antiviral), and antihistamines. All suitable combinations are envisaged.

Suitable anti-inflammatory agents include corticosteroids and NSAIDs. Suitable corticosteroids are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl) oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), feukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Suitable phosphodiesterase 4 (PDE4) inhibitors include compounds that are known to inhibit the PDE4 enzyme or which are discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$s ratios is set out in U.S. Pat. No. 5,998,428 which is incorporated herein in full by reference as though set out herein. See also PCT application WO 00/51599 for an another description of said assay.

Suitable PDE4 inhibitors include those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Most suitable are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other suitable medicament compounds include: cis-4-cyano-4-[3-(cyclopentyloxy)-4-methoxyphenyl]cyclohexane-1-carboxylic acid (also known as cilomalast) disclosed in U.S. Pat. No. 5,552,438 and its salts, esters, pro-drugs or physical forms; AWD-12-281 from elbion (Hofgen, N. et al. 15th EFMC Int Symp Med Chem (Sep. 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sep. 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-methoxy-8-methoxy-2-methylbenzo[c][1,6] naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Suitable anticholinergic agents are those compounds that act as antagonists at the muscarinic receptor, in particular those compounds, which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines.

Particularly suitable anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCI, and tripelennamine citrate.

Alkylamines: chlropheniramine and its salts such as the maleate salt, and acrivastine.

Piperazines: hydroxyzine HCI, hydroxyzine pamoate, cyclizine HCI, cyclizine lactate, meclizine HCI, and cetirizine HCI.

Piperidines: Astemizole, levocabastine HCI, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Particularly suitable anti-histamines include methapyrilene and loratadine.

In respect of combination products, co-formulation compatibility is generally determined on an experimental basis by known methods and may depend on chosen type of medicament dispenser action.

The medicament components of a combination product are suitably selected from the group consisting of anti-inflammatory agents (for example a corticosteroid or an NSAID), anticholinergic agents (for example, an $M_1$, $M_2$, $M_1/M_2$ or $M_3$ receptor antagonist), other $\beta_2$-adrenoreceptor agonists, antiinfective agents (e.g. an antibiotic or an antiviral), and antihistamines. All suitable combinations are envisaged.

Suitably, the co-formulation compatible components comprise a $\beta_2$-adrenoreceptor agonist and a corticosteroid; and the co-formulation incompatible component comprises a PDE-4 inhibitor, an anti-cholinergic or a mixture thereof. The $\beta_2$-adrenoreceptor agonists may for example be salbutamol (e.g., as the free base or the sulphate salt) or salmeterol (e.g., as the xinafoate salt) or formoterol (eg as the fumarate salt). The corticosteroid may for example, be a beclomethasone ester (e.g., the dipropionate) or a fluticasone ester (e.g., the propionate) or budesonide.

In one example, the co-formulation compatible components comprise fluticasone propionate and salmeterol, or a salt thereof (particularly the xinafoate salt) and the co-formulation incompatible component comprises a PDE-4 inhibitor, an anti-cholinergic (e.g. ipratropium bromide or tiotropium bromide) or a mixture thereof.

In another example, the co-formulation compatible components comprise budesonide and formoterol (e.g. as the fumarate salt) and the co-formulation incompatible component comprises a PDE-4 inhibitor, an anti-cholinergic (e.g. ipratropium bromide or tiotropium bromide) or a mixture thereof.

Generally, powdered medicament particles suitable for delivery to the bronchial or alveolar region of the lung have an aerodynamic diameter of less than 10 micrometers, preferably from 1-6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

The medicament dispenser of the invention is in one aspect suitable for dispensing medicament for the treatment of respiratory disorders such as disorders of the lungs and bronchial tracts including asthma and chronic obstructive pulmonary disorder (COPD). In another aspect, the medicament dispenser of the invention is suitable for dispensing medicament for the treatment of a condition requiring treatment by the systemic circulation of medicament, for example migraine, diabetes, pain relief e.g. inhaled morphine.

Accordingly, there is provided the use of the medicament dispenser herein for the treatment of a respiratory disorder, such as asthma and COPD. Alternatively, the present invention provides a method of treating a respiratory disorder such as, for example, asthma and COPD, which comprises administration by inhalation of an effective amount of medicament product as herein described from a medicament dispenser herein.

The amount of any particular medicament compound or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The medicaments for treatment of respiratory disorders herein may for example, be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1 mg per day.

It will be understood that the present disclosure is for the purpose of illustration only and the invention extends to modifications, variations and improvements thereto.

All documents referred to herein are hereby incorporated herein by reference in their entirety.

The invention claimed is:

1. A medicament dispenser for use with at least one medicament carrier carrying multiple distinct medicament portions, said medicament dispenser comprising (a) a dispensing mechanism actuable for dispensing the distinct medicament portions carried by said at least one medicament carrier;

(b) a mouthpiece; and (c) a cover for said mouthpiece, said cover being movably mounted to the dispenser for sequential movement from a first position, in which said mouthpiece is covered, to a second position, in which said mouthpiece is part-uncovered, to a third position in which said mouthpiece is uncovered;

wherein said cover is adapted to couple with said dispensing mechanism such that movement of the cover from the first position to the second position does not result in actuation of the dispensing mechanism, but any further movement of the cover from the second position to the third position results in actuation of the dispensing mechanism.

2. A medicament dispenser according to claim 1 including a plurality of said medicament carriers each carrying multiple distinct medicament dose portions.

3. A medicament dispenser according to claim 2 wherein the dispenser is an inhalation device, the medicament dose portions of each carrier are in powdered form and the dispenser is adapted such as to enable a user to inhale at the mouthpiece for simultaneous inhalation by the user of the medicament dose portions dispensed from the medicament carriers by the dispensing mechanism on actuation thereof by movement of the cover from the second position to the third position.

4. A medicament dispenser according to claim 2, wherein said plurality of said medicament carriers consists of a first and a second medicament carrier, each of said medicament carriers carrying distinct medicament portions in powder form, each of said medicament dose portions of said first medicament carrier comprising a bronchodilator as the active medicament component and each of said medicament dose portions of said second medicament carrier comprising an anti-inflammatory as the active medicament component.

5. A medicament dispenser according to claim 4, wherein said bronchodilator is a beta-agonist and said anti-inflammatory is a corticosteroid.

6. A medicament dispenser according to claim 1, wherein said at least one medicament carrier is an elongate form medicament carrier.

7. A medicament dispenser according to claim 1, wherein said dispensing mechanism comprises:

i) a receiving station for receiving each medicament carrier;

ii) a release for releasing a distinct medicament portion from each medicament carrier on receipt thereof by said receiving station;

iii) an outlet for communication with the mouthpiece and with said distinct medicament portion of each medicament carrier releasable by said release; and iv) an indexer for individually indexing the distinct medicament portions of each medicament carrier.

8. A medicament dispenser according to claim 7, for use with at least one blister strip form medicament carrier, the at least one blister strip form medicament carrier having multiple distinct pockets for containing medicament dose portions, wherein said pockets are spaced along the length of and defined between two peelable sheets secured to each other, and in which the release comprises a peeler positioned to engage a base sheet and a lid sheet of a pocket which has been received in said receiving station for peeling apart such a base sheet and lid sheet, to open such a pocket.

9. A medicament dispenser according to claim 1, wherein the cover couples directly with the dispensing mechanism.

10. A medicament dispenser according to claim 1, wherein the cover couples mechanically with the dispensing mechanism.

11. A medicament dispenser according to claim 10 wherein the housing defines an inlet for the mouthpiece arranged such that the inlet is covered by the mouthpiece cover in its first position, part-uncovered by the mouthpiece cover in its second position and fully revealed when the mouthpiece cover is in its third position.

12. A medicament dispenser according to claim 1, further comprising a housing, wherein the dispensing mechanism is within the housing and the cover is in movable connection with the housing.

13. A medicament dispenser according to claim 1, wherein the cover is arranged for movement on a rotational path.

14. A medicament dispenser according to claim 1, wherein the cover interacts with a ratchet of the dispensing mechanism, which in turn selectively interacts with a drive gear of the dispensing mechanism for drive of the dispensing mechanism.

15. A medicament dispenser according to claim 14, adapted such that on movement of the cover from the first position until the second position the ratchet is disengaged from the drive gear and on movement from the second position to the third position the ratchet is in engagement with the drive gear.

16. A medicament dispenser according to claim 14, wherein the dispensing mechanism is provided with an anti-return feature to prevent return movement of the drive gear on return movement of the cover from the third position to the first position.

17. A medicament dispenser according to claim 14, wherein the ratchet and drive gear are respectively provided with at least one first and second ratchet feature for providing unidirectional driving engagement of the ratchet and drive gear.

18. A medicament dispenser according to claim 17, wherein the at least one first and second ratchet feature are constructed and arranged such that they are disengaged except when the cover is positioned from the second position to the third position after moving the cover towards the third position.

19. A medicament dispenser according to claim 14, wherein the cover is connected to the ratchet.

20. A medicament dispenser according to claim 1, wherein the at least one medicament carrier carries distinct medicament portions in powder form.

21. A medicament dispenser according to claim 20, comprising a single medicament carrier wherein each medicament portion comprises both a bronchodilator and an anti-inflammatory as active medicament components thereof.

22. A medicament dispenser according to claim 21, wherein said bronchodilator is a beta-agonist and said anti-inflammatory is a corticosteroid.

23. A medicament dispenser according to claim 1, wherein the coupling of the cover with the dispensing mechanism is adapted such that only movement of the cover from the second position to the third position results in actuation of the dispensing mechanism.

24. A medicament dispenser according to claim 23, wherein the dispensing mechanism comprises a first part to which the cover is connected and which moves with the cover, a second part drivable by the first part to operate on the at least one medicament carrier for dispensing of the distinct medicament portions, and an interface between the first and second parts which is adapted so that the first part is only able to drive the second part when the cover moves from the second position to the third position.

25. A medicament dispenser according to claim 24, wherein the interface is formed by a ratchet arrangement.

26. A medicament dispenser according to claim 25, wherein the ratchet arrangement comprises a ratchet and a drive gear.

27. A medicament dispenser according to claim 26, wherein the ratchet and drive gear are respectively provided with at least one first and second ratchet feature for providing unidirectional driving engagement of the ratchet and drive gear.

28. A medicament dispenser according to claim 27, wherein the at least one first and second ratchet feature are constructed and arranged such that they are disengaged except when the cover is positioned from the second position to the third position after moving the cover towards the third position.

29. A medicament dispenser according to claim 25, wherein the ratchet arrangement has first and second components respectively provided with at least one first and second ratchet feature for providing unidirectional driving engagement between the first and second components.

30. A medicament dispenser according to claim 29, wherein the cover is connected to the first component.

*31. A medicament dispenser according to claim 1 including a single medicament carrier carrying multiple distinct medicament dose portions.*

*32. A medicament dispenser according to claim 31, wherein said medicament carrier carries distinct medicament portions in powder form, each of said medicament dose portions comprising an anti-inflammatory.*

*33. A medicament dispenser according to claim 32 wherein said anti-inflammatory is a corticosteroid.*

*34. A medicament dispenser according to claim 33, wherein said corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.*

*35. A medicament dispenser according to claim 5 wherein said corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.*

*36. A medicament dispenser according to claim 2, wherein said plurality of said medicament carriers consists of a first and a second medicament carrier each of said medicament carriers carrying distinct medicament portions in powder form, each of said medicament dose portions of said first medicament carrier comprising a bronchodilator and each of said medicament dose portions of said second medicament carrier comprising an anti-inflammatory.*

*37. A medicament dispenser according to claim 36 wherein said bronchodilator is a beta-agonist and said anti-inflammatory is a corticosteroid.*

*38. A medicament dispenser according to claim 37 wherein said corticosteroid is 6α,9α-difluoro-17α-[(2-fura-*

*nylcarbonyl)oxy]-11β-hydroxy-16α-methyl-3-oxo-androsta-1,4-diene-17β-carbothioic acid S-fluoromethyl ester.*

* * * * *